US010232345B2

(12) United States Patent
Rege et al.

(10) Patent No.: US 10,232,345 B2
(45) Date of Patent: Mar. 19, 2019

(54) AMINOGLYCOSIDE HYDROGEL MICROBEADS AND MACROPOROUS GELS WITH CHEMICAL CROSSLINK, METHOD OF PREPARATION AND USE THEREOF

(71) Applicant: ARIZONA BOARD OF REGENTS ON BEHALF OF ARIZONA STATE UNIVERSITY, Scottsdale, AZ (US)

(72) Inventors: Kaushal Rege, Chandler, AZ (US); Taraka Sai Pavan Grandhi, Tempe, AZ (US); Thrimoorthy Potta, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/547,173

(22) PCT Filed: Feb. 12, 2016

(86) PCT No.: PCT/US2016/017771
§ 371 (c)(1),
(2) Date: Jul. 28, 2017

(87) PCT Pub. No.: WO2016/130928
PCT Pub. Date: Aug. 18, 2016

(65) Prior Publication Data
US 2018/0021753 A1 Jan. 25, 2018

Related U.S. Application Data

(60) Provisional application No. 62/115,392, filed on Feb. 12, 2015.

(51) Int. Cl.
| | |
|---|---|
| B01J 20/285 | (2006.01) |
| B01D 15/20 | (2006.01) |
| B01J 20/26 | (2006.01) |
| B01J 20/28 | (2006.01) |
| C12N 15/10 | (2006.01) |
| G01N 30/52 | (2006.01) |

(52) U.S. Cl.
CPC ........... *B01J 20/285* (2013.01); *B01D 15/20* (2013.01); *B01J 20/267* (2013.01); *B01J 20/28052* (2013.01); *C12N 15/101* (2013.01); *G01N 2030/528* (2013.01)

(58) Field of Classification Search
CPC . B01J 20/285; B01J 20/28025; C12N 15/101; B01D 15/20
See application file for complete search history.

(56) References Cited

U.S. PATENT DOCUMENTS

| 3,860,574 | A | 1/1975 | Naito et al. |
|---|---|---|---|
| 3,984,393 | A | 10/1976 | Magerlein |
| 4,347,354 | A | 8/1982 | Cron et al. |
| 5,151,264 | A | 9/1992 | Saimain |
| 9,801,954 | B2 | 10/2017 | Rege et al. |
| 9,856,332 | B2 | 1/2018 | Rege et al. |
| 2002/0130082 | A1 | 9/2002 | Todokoro et al. |
| 2007/0298006 | A1 | 12/2007 | Tomalia et al. |
| 2008/0207535 | A1 | 8/2008 | Urban et al. |
| 2009/0282496 | A1 | 11/2009 | Chang |
| 2010/0143487 | A1 | 6/2010 | Masters |
| 2012/0034627 | A1 | 2/2012 | Singh |
| 2012/0196923 | A1 | 8/2012 | Rege et al. |
| 2014/0079752 | A1 | 3/2014 | Huebsch et al. |
| 2015/0212071 | A1 | 7/2015 | Berry et al. |
| 2015/0283073 | A1 | 10/2015 | Tang |
| 2016/0228611 | A1 | 8/2016 | Castro et al. |
| 2017/0115275 | A1 | 4/2017 | Rege et al. |
| 2017/0232157 | A1 | 8/2017 | Rege et al. |
| 2018/0258416 | A1 | 9/2018 | Rege et al. |

FOREIGN PATENT DOCUMENTS

| EP | 0224987 A2 | 6/1987 |
|---|---|---|
| WO | 1999028308 A1 | 6/1999 |
| WO | 2005027873 A2 | 3/2005 |
| WO | 2010132876 A1 | 11/2010 |
| WO | 2013055971 A1 | 4/2013 |
| WO | 2014022749 A1 | 2/2014 |
| WO | 2014066674 A1 | 5/2014 |
| WO | 2015069694 A1 | 5/2015 |
| WO | 2016130928 A1 | 8/2016 |
| WO | 2017161100 A1 | 9/2017 |

OTHER PUBLICATIONS

Woodgate, J. et al., "Protein-mediated isolation of plasmid DNA by a zinc finger-glutathione S-transferase affinity inker", Biotechnology and Bioengineering, Aug. 2002 (epub Jun. 2002), 79(4), pp. 450-456.
Wu, J. et al., "Extraction, amplification and detection of DNA in microfluidic chip-based assays", Microchimica Acta, Oct. 2014 (epub Dec. 2013), 181(13-14), pp. 1611-1631.
Xiong, X. et al., "Responsive DNA-based hydrogels and their applications", Macromolecular Rapid Communications, Aug. 2013 (epub Jul. 2013), 34(16), pp. 1271-1283.
Xiong, Y., et al, "Synaptic transmission of neural stem cells seeded in 3-dimensional PLGA scaffolds", Biomaterials, Aug. 2009 (epub Apr. 2009), 30(22), pp. 3711-3722.

(Continued)

*Primary Examiner* — Robert S Jones
(74) *Attorney, Agent, or Firm* — Gavin J. Milczarek-Desai; Quarles & Brady LLP

(57) ABSTRACT

Methods and materials for the generation of amikacin antibiotic-derived microbeads, (FIG. 3). These beads may function as anion-exchange resins for use in pDNA purification as well as in situ capture of DNA from mammalian cells. New microresin and macroporous monolith based materials also are disclosed and may function for plasmid DNA binding and purification, mammalian whole cell genomic DNA extraction, and in-vitro cell culture.

22 Claims, 26 Drawing Sheets

(56) References Cited

OTHER PUBLICATIONS

Yue, Z. et al, "Preparation of three-dimensional interconnected macroporous cellulosic hydrogels for soft tissue engineering", Biomaterials, Nov. 2010 (epub Aug. 2010), 31(32), pp. 8141-8152.

Zeng, W. et al., "Ionically cross-linked chitosan microspheres for controlled release of bioactive nerve growth factor", International Journal of Pharmaceutics, Dec. 2011 (epub Oct. 2011), 421(2), pp. 283-290.

Marks, M. et al.,"In Vitro Antibacterial Activity of Amikacin, a New Aminoglycoside, Against Clinical Bacterial Isolates from Children", Journal of Clinical Pharmacology, Apr. 1975, 15(4), pp. 246-251.

Alton, E. et al., "Non-invasive liposome-mediated gene delivery can correct the ion transport defect in cystic fibrosis mutant mice", Nature Genetics, Oct. 1993, 5, pp. 135-142.

Anderson, W., "Prospects for human gene therapy", Science, Oct. 1984, 226(4673), pp. 401-409.

Arya, D. et al., "Aminoglycoside-Nucleic Acid Interactions: Remarkable Stabilization of DNA and RNA Triple Helices by Neomycin", Journal of the American Chemical Society, Jun. 2001 (epub May 2001), 123(23), pp. 5385-5395.

Banerjee, R. et al., "Plasmid DNA-Mediated Gene Therapy", Burger's Medicinal Chemistry and Drug Discovery, 2003, 4, 641-667.

Bodamer, G. et al., "Behavior of Ion Exchange Resins in Solvents Other Than Water—Swelling and Exchange Characteristics", Industrial & Engineering Chemistry, 1953, 45(11), pp. 2577-2580.

Boussif, O., et al., "A versatile vector for gene and oligonucleotide transfer into cells in culture and in vivo: polyethylenimine", PNAS USA, Aug. 1995, 92(16), pp. 7297-7301.

Brownlie, A. et al., "PEI-based vesicle-polymer hybrid gene delivery system with improved biocompatibility", International Journal of Pharmaceutics, Apr. 2004 (epub Mar. 2004), 274(1-2), pp. 41-52.

Cao, W. et al., "Chitosan as a polymer for pH-induced DNA capture in a totally aqueous system", Analytical Chemistry, Oct. 2006 (epub Sep. 2006), 78(20), pp. 7222-7228.

Chan, V. et al., "Effect of Hydrophobicity and Electrostatics on Adsorption and Surface Diffusion of DNA Oligonucleotides at Liquid/Solid Interfaces", Journal of Colloid and Interface Science, Jul. 1998, 203(1), pp. 197-207.

Chang, C. et al., "Preparation of inorganic-organic anion-exchange membranes and their application in plasmid DNA and RNA separation", Journal of Membrane Science, Mar. 2008 (epub Dec. 2007), 311(1-2), pp. 336-348.

Cohen, S. et al., "Nonchromosomal Antibiotic Resistance in Bacteria: Genetic Transformation of *Escherichia coli* by R-Factor DNA", PNAS USA, Aug. 1972, 69(8), pp. 2110-2114.

Corr, M. et al., "Gene vaccination with naked plasmid DNA: mechanism of CTL priming", Journal of Experimental Medicine, Oct. 1996, 184(4), pp. 1555-1560.

Costa, D. et al., "Plasmid DNA hydrogels for biomedical applications", Advances in Colloid and Interface Science, Mar. 2014 (epub Aug. 2013), 205, pp. 257-264.

Diogo, M. et al., "Chromatography of plasmid DNA", Journal of Chromatography A, Mar. 2005, 1069(1), pp. 3-22.

Diogo, M. et al., "Scale-up of hydrophobic interaction chromatography for the purification of a DNA vaccine against rabies", Biotechnology Letters, Sep. 2000, 22(17), pp. 1397-1400.

Diogo, M. et al., "Studies on the retention of plasmid DNA and *Escherichia coil* nucleic acids by hydrophobic Interaction chromatography", Bioseparation, May 2001, 10(4-5), pp. 211-220.

Discher, D. et al., "Growth Factors, Matrices, and Forces Combine and Control Stem Cells", Science, Jun. 2009, 324(5953), pp. 1673-1677.

Elmer, J. et al., "Applying horizontal gene transfer phenomena to enhance non-viral gene therapy", Journal of Controlled Release, Nov. 2013 (epub Aug. 2013), 172(1), pp. 246-257.

Eon-Duval, A. et al., "Purification of pharmaceutical-grade plasmid DNA by anion-exchange chromatography in an RNase-free process", Journal of Chromatography B, May 2004 (epub Feb. 2004), 804(2), pp. 327-335.

Flaibani, M. et al. ,"Gas anti-solvent precipitation assisted salt leaching for generation of micro- and nano-porous wall in biopolymeric 3D scaffolds", Materials Science and Engineering C, Aug. 2012 (epub Apr. 2012), 32(6), pp. 1632-1639.

Glazer, A. et al., "A stable double-stranded DNA-ethidium homodimer complex: application to picogram fluorescence detection of DNA in agarose gels", PNAS USA, May 1990, 87(10), pp. 3851-3855.

Grandhi, T. et al, "Aminoglycoside Antibiotic-Derived Anion-Exchange Microbeads for Plasmid DNA Binding and in Situ DNA Capture", ACS Applied Materials & Interfaces, Oct. 2014, 6(21), pp. 18577-18589.

Grandhi, T. et al, "Design of Bone Microenvironment Mimicking Antibiotic-based Hydrogels for Generation of Three Dimensional Tumor Models of Dormancy and Relapse", 2014 Society for Biomaterials Annual Meeting & Exposition, Apr. 16-19, 2014, Denver, CO, Abstract 191.

Grandhi, T. et al, "Generation of 3D tissue models of tumor dormancy and relapse using bone microenvironment mimicking antibiotics-derived hydrogels", 247th ACS National Meeting and Exposition, Dallas, TX, USA, Mar. 16-20, 2014, Abstract BIOT-119, obtained on Sep. 24, 2018 from ACS website <http://acselb-529643017.us-west-2.elb.amazonaws.com/chem/247nm/program/view.php?obj_id=242822&terms=>.

Grandhi, T. et aL, "High-Throughput Amikagel Platform for Identification of Synergistic Treatments Against Tumor Dormancy", 2015 AiChE Annual Meeting, Nov. 8-13, 2015, Salt Lake City, UT, Abstract 433581, obtained on Sep. 24, 2018 from AiChE website <https://aiche.confex.com/aiche/2015/webprogram/Paper433581.html>.

Gruskiene, R. et al., "Quaternization of chitosan and partial destruction of the quaternized derivatives making them suitable for electrospinning", Chemjia, 2013, 24(4), 325-334.

Guan, L. et al., "Preparation and characterization of a highly macroporous biodegradable composite tissue engineering scaffold", Journal of Biomedical Materials Research Part A, Dec. 2004 (epub Oct. 2004), 71A(3), 480-487.

Hedhammer, M. et al., "Chromatographic methods for protein purification", Royal Institute of Technology, AlbaNova University Center, Dept. Of Biotechnology, SE-106 91 Stockholm, Sweden, 2006.

Henry, M. et al., "Spiculated Periosteal Response Induced by Intraosseous Injection of 22Rv1Prostate Cancer Cells Resembles Subset of Bone Metastases in Prostate Cancer Patients", The Prostate, 2005, 65, pp. 347-354.

Hermanson, G. et al., "A cationic lipid-formulated plasmid DNA vaccine confers sustained antibody-mediated protection against aerosolized anthrax spores", PNAS USA, Sep. 2004, 101(37), pp. 13601-13606.

Horn, N. et al., "Cancer gene therapy using plasmid DNA: purification of DNA for human clinical trials", Human Gene Therapy, May 1995, 6(5), pp. 565-573.

Huang, H. et al., "Simultaneous Enhancement of Photothermal Stability and Gene Delivery Efficacy of Gold Nanorods Using Polyelectrolytes", ACS Nano, Sep. 2009 (Correction Feb. 2010), 3(10), pp. 2941-2952.

Iuliano, S. et al., "Rapid analysis of a plasmid by hydrophobic-interaction chromatography with a non-porous resin", Journal of Chromatography A, Sep. 2002 (epub Aug. 2002), 972(1), 77-86.

Kean, T. et al., "Trimethylated chitosans as non-viral gene delivery vectors: Cytotoxicity and transfection efficiency", Journal of Controlled Release, Apr. 2005 (epub Feb. 2005), 103(3), pp. 643-653.

Khademhosseini, A. et al., "Microengineered hydrogels for tissue engineering", Biomaterials, Dec. 2007 (epub Aug. 2007), 28(34), pp. 5087-5092.

Kim, J. et al., "Microfluidic sample preparation: cell lysis and nucleic acid purification", Integrative Biology, Oct. 2009 (epub Aug. 2009), 1, pp. 574-586.

(56) References Cited

OTHER PUBLICATIONS

Koga, Y. et al., "Is a Methyl Group Always Hydrophobic? Hydrophilicity of Trimethylamine-N-oxide, Tetramethyl Urea and Tetramethylammonium Ion", Journal of Physical Chemistry B, Mar. 2011, 115(12), pp. 2995-3002.

Kotra, L. et al., "Aminoglycosides: Perspectives on Mechanisms of Action and Resistance and Strategies to Counter Resistance", Antimicrobial Agents and Chemotherapy, Dec. 2000, 44(12), pp. 3249-3256.

Lao, U. U et al, "Affinity purification of plasmid DNA by temperature-triggered precipitation", Nature Protocols, May 2007, 2(5), pp. 1263-1268.

Latulippe, D. et al., "Flux-dependent transmission of supercoiled plasmid DNA through ultrafiltration membranes", Journal of Membrane Science, May 2007 (epub Feb. 2007), 294(1-2), pp. 169-177.

Lee, H. et al, "Enhancement of cell viability by fabrication of macroscopic 3D hydrogel scaffolds using an innovative cell-dispensing technique supplemented by preosteoblast-laden microbeads", Carbohydrate Polymers, Apr. 2014 (epub Jan. 2014), 104, pp. 191-198.

Lee, H. et al, "Fabrication and Characteristics and Anti-Inflammatory Magnesium Hydroxide Incorporated PLGA Scaffolds Formed with Various Porogen Materials", Macromolecular Research, Feb. 2014 (epub Dec. 2013), 22(2), pp. 210-218.

Lee, J. et al.' "Polyplexes Assembled with Internally Quaternized PAMAM-OH Dendrimer and Plasmid DNA Have a Neutral Surface and Gene Delivery Potency", Bioconjugate Chemistry, Nov. 2003, 14(6), pp. 1214-1221.

Lee, J. et al., "Quaternized Polyamidoamine Dendrimers as Novel Gene Delivery System: Relationship between Degree of Quaternization and Their Influences", Bulletin- Korean Chemical Society, 2003, 24(11), pp. 1637-1640.

Limonta, M. et al., "Plasmid DNA Recovery Using Size-Exclusion and Perfusion Chromatography", Biopharm International, Sep. 2008, 21(9), pp. 38-41.

Lin, H. et al., "Preparation of macroporous biodegradable PLGA scaffolds for cell attachment with the use of mixed salts as porogen additives", Journal of Biomedical Materials Research, Jul. 2002, 63(3), pp. 271-279.

Lodish, H. et al., "Biomembranes: Structural Organization and Basic Functions", Molecular Cell Biology (eds. Lodish, H., Berk, A., Zipursky S.L.), 4th Edition, 2000, New York: W.M. Freeman.

Lundberg, J. et al, "Affinity purification of specific DNA fragments using a lac repressor fusion protein", Gene Analysis Techniques, May 1990, 7(3), pp. 47-52.

Mallik, A., "Preparation and Evaluation of Aminoglycoside-Based Nanogels and Microgels for Gene Delivery and DNA binding", Masters Thesis, May 2014, ASU Respository, 32 pages.

McCaldin, D., "The Chemistry of Ninhydrin", Chemical Reviews, 1960, 60(1), pp. 39-51.

Mehta, G. et al., "Opportunities and challenges for use of tumor spheroids as models to test drug delivery and efficacy", Journal of Controlled Release, Dec. 2012 (epub May 2012), 164(2), pp. 192-204.

Mehta, R. et al., "30S Ribosomal Subunit Assembly Is a Target for Inhibition by Aminoglycosides in *Escherichia coli*", Antimicrobial Agents and Chemotherapy, May 2002, 46(5), pp. 1546-1549.

Mi, Y. et al., "Fabrication of porous synthetic polymer scaffolds for tissue engineering", Journal of Cellular Plastics, Mar. 2015 (epub Apr. 2014), 51(2), pp. 165-196.

Murphy, W. et al., "Salt fusion: an approach to improve pore interconnectivity within tissue engineering scaffolds", Tissue Engineering, Feb. 2002, 8(1), pp. 43-52.

Niemz, A et al., "Point-of-care nucleic acid testing for infectious diseases", Trends in Biotechnology, May 2011 (epub Mar. 2011), 29(5), pp. 240-250.

Paez, D et al., "Cancer Dormancy: A Model of Early Dissemination and Late Cancer Recurrence", Clinical Cancer Research, Feb. 2012 (epub Dec. 2011), 18(3), pp. 645-653.

Palermo, E. et al., "Chemical Structure of Cationic Groups in Amphiphilic Polymethacrylates Modulates the Antimicrobial and Hemolytic Activities", Biomacromolecules, Apr. 2009, 10(6), pp. 1416-1428.

Palermo, E. et al., "Role of Cationic Group Structure in Membrane Binding and Disruption by Amphiphilic Copolymers", Journal of Physical Chemistry B, 2011 (epub Dec. 2010), 115(2), pp. 366-375.

Park, H. et al.,"Effect of Swelling Ratio of Injectable Hydrogel Composites on Chondrogenic Differentiation of Encapsulated Rabbit Marrow Mesenchymal Stem Cells in Vitro", Biomacromolecules, Jan. 2009, 10(3), pp. 541-546.

Patent Cooperation Treaty, International Searching Authority, International Preliminary Report and Patentability and Written Opinion for PCT/US2012/059828, 5 pages, dated Apr. 15, 2014, Opinion dated Feb. 26, 2013.

Patent Cooperation Treaty, International Searching Authority, International Preliminary Report and Patentability and Written Opinion for PCT/US2014/064017, 5 pages, dated May 10, 2016, Opinion dated Jan. 21, 2015.

Patent Cooperation Treaty, International Searching Authority, International Preliminary Report and Patentability and Written Opinion for PCT/US2016/017771, 7 pages, dated Aug. 15, 2017, Opinion dated Jul. 1, 2016.

Patent Cooperation Treaty, International Searching Authority, International Search Report for PCT/US2012/059828, 5 pages, dated Feb. 26, 2013.

Patent Cooperation Treaty, International Searching Authority, International Search Report for PCT/US2014/064017, 2 pages, dated Jan. 21, 2015.

Patent Cooperation Treaty, International Searching Authority, International Search Report for PCT/US2016/017771, 4 pages, dated Jul. 1, 2016.

Patent Cooperation Treaty, International Searching Authority, International Search Report for PCT/US2017/022675, 3 pages, dated Jun. 8, 2017.

Patent Cooperation Treaty, International Searching Authority, Written Opinion for PCT/US2017/022675, 6 pages, dated Jun. 8, 2017.

Peppas, N. et al, "Hydrogels in Biology and Medicine: From Molecular Principles to Bionanotechnology", Advanced Materials, May 2006, 18(11), pp. 1345-1360.

Potta, T. et al., "Discovery of antibiotics-derived polymers for gene delivery using combinatorial synthesis and cheminformatics modeling", Biomaterials, Feb. 2014 (epub Dec. 2013), 35(6), pp. 1977-1988.

Prazeres, D. et al., "Preparative purification of supercoiled plasmid DNA using anion-exchange chromatography", Journal of Chromatography A, May 1998, 806(1), pp. 31-45.

Rege, K. et al, "Chemoenzymatic Synthesis and High-Throughput Screening of an Aminoglycoside-Polyamine Library: Identification of High-Affinity Displacers and DNA-Binding Ligands", Journal of the American Chemical Society, Sep. 2004, 126(39), pp. 12306-12315.

Rege, K. et al, "Investigation of DNA-binding properties of an aminoglycoside-polyamine library using quantitative structure-activity relationship (QSAR) models", Journal of Chemical Information and Modeling, Nov.-Dec. 2005 (epub Oct. 2005), 45(6), pp. 1854-1863.

Rigaud, J. et al., "Prognostic Value of Bone Scan in Patients With Metastatic Prostate Cancer Treated Initially With Androgen Deprivation Therapy", Journal of Urology, Oct. 2002, 168(4)(1), pp. 1423-1426.

Rodriguez, M. et al., "Combined effect of plasticizers and surfactants on the physical properties of starch based edible films", Food Research International, Oct. 2006, 39(8), pp. 840-846.

Sheikh, N. et al., "A study on the swelling behavior of poly(acrylic acid) hydrogels obtained by electron beam crosslinking", Radiation Physics and Chemistry, Jun. 2010, 79(6), pp. 735-739.

Siegel, R. et al., "Cancer statistics, 2014", CA: A Cancer Journal for Clinicians, Jan.-Feb. 2014 (epub Jan. 2014), 64(1), pp. 9-29.

Sousa, F. et al., "Affinity chromatography approaches to overcome the challenges of purifying plasmid DNA", Trends in Biotechnology, Sep. 2008 (epub Jul. 2008), 26(9), pp. 518-525.

(56) References Cited

OTHER PUBLICATIONS

Sousa, F. et al., "Specific recognition of supercoiled plasmid DNA in arginine affinity chromatography", Analytical Biochemistry, Mar. 2008 (epub Nov. 2007), 374(2), pp. 432-434.
Talebi, M. et al., "Epoxy-based monoliths for capillary liquid chromatography of small and large molecules", Analytical and Bioanalytical Chemistry, Mar. 2013 (epub Nov. 2012), 405(7), pp. 2233-2244.
Tan, Q. et al., "Fabrication of porous scaffolds with a controllable microstructure and mechanical properties by porogen fusion technique", International Journal of Molecular Sciences, Jan. 2011, 12(2), pp. 890-904.
Tighe, H. et al., "Gene vaccination: plasmid DNA is more than just a blueprint", Immunology Today, Feb. 1998, 19(2), pp. 89-97.
Tiihonen, J. et al., "Elasticity of Ion-Exchange Resin Beads in Solvent Mixtures", Journal of Applied Polymer Science, Aug. 2001, 82(5), pp. 1256-1264.
Tiller, J. et al., "Designing surfaces that kill bacteria on contact", PNAS USA, May 2001, 98(11), pp. 5981-5985.
To, B. et al., "Hydrophobic interaction chromatography of proteins. I. The effects of protein and adsorbent properties on retention and recovery", Journal of Chromatography A, Feb. 2007 (epub Jan. 2007), 1141(2), pp. 191-205.
Tokuyama, H. et al., "Preparation of poly(N-isopropylacrylamide) hydrogel beads by circulation polymerization", Reactive and Functional Polymers, Dec. 2010 (epub Oct. 2010), 70(12), pp. 967-971.
Tombal, B. et al., "Modem Detection of Prostate Cancer's Bone Metastasis: Is the Bone Scan Era Over?", Advances in Urology, 2012 (epub Oct. 2011), article ID 893193, 8 pages, doi: 10.1155/2012/893193.
Tseng, W. et al., "Effect of alcohol on purification of plasmid DNA using ion-exchange membrane", Journal of Membrane Science, Apr. 2004 (epub Mar. 2004), 233(1-2), 161-16T.
Tseng, W. et al., "Enhanced purification of plasmid DNA using Q-Sepharose by modulation of alcohol concentrations", Journal of Chromatography B, Jul. 2003 (epub Apr. 2003), 791(1-2), pp. 263-272.
U.S. Appl. No. 14/065,068, filed Oct. 28, 2013.
USPTO, Final Office Action for U.S. Appl. No. 14/065,068, dated Dec. 18, 2014.
USPTO, Final Office Action for U.S. Appl. No. 14/065,068, dated Jul. 8, 2015.
USPTO, Non-Final Office Action for U.S. Appl. No. 14/065,068, dated Jul. 7, 2014.
USPTO, Non-Final Office Action for U.S. Appl. No. 15/034,425, dated Feb. 6, 2017.
USPTO, Non-Final Office Action for U.S. Appl. No. 15/077,743, dated May 9, 2017.
USPTO, Non-Final Office Action for U.S. Appl. No. 15/332,928, dated Aug. 31, 2018.
Voordouw, G. et al., "Isolation and physical studies of the intact supercoiled: The open circular and the linear forms of ColE1-plasmid DNA", Biophysical Chemistry, May 1978, 8(2), pp. 171-189.
Vozzi, G. et al., "Fabrication of PLGA scaffolds using soft lithography and microsyringe deposition", Biomaterials, Jun. 2003 (epub Mar. 2003), 24(14), pp. 2533-2540.
Wells, A. et al., "The dormancy dilemma: quiescence versus balanced proliferation", Cancer Research, Jul. 2013 (epub Jun. 2013), 73(13), pp. 3811-3816.
Wikman, H. et al., "Cancer micrometastasis and tumour dormancy", APMIS, Jul.-Aug. 2008, 116(7-8), pp. 754-770.
Wils, P. et al., "Efficient purification of plasmid DNA for gene transfer using triple-helix affinity chromatography", Gene Therapy, Apr. 1997, 4(4), pp. 323-330.

| ID | Aminoglycoside |
|---|---|
| 1 | Amikacin |
| 2 | Neomycin |
| 3 | Streptomycin |
| 4 | Tobramycin |
| 5 | Sisomicin |
| 6 | Paromomycin |
| 7 | Apramycin |
| 8 | Framecytin |
| 9 | Ribostamycin |
| 10 | Kanamycin |
| 11 | Arbekacin |
| 12 | Beckanamycin |
| 13 | Dibekacin |
| 14 | Astromicin |
| 15 | Spectinomycin |
| 16 | Hygromycin b |
| 17 | Gentamicin |
| 18 | Netilmicin |
| 19 | Isepamicin |
| 20 | Verdamicin |

Fig. 1

| ID | Crosslinker |
|---|---|
| 1 | Poly (ethylene glycol) diglycidyl ether |
| 2 | Ethylene glycol diglycidyl ether |
| 3 | 1,4-Cyclohexane dimethanol diglycidyl ether |
| 4 | Neopentyl glycol diglycidyl ether |
| 5 | 1,4- Butanediol diglycidyl ether |
| 6 | Resorcinol diglycidyl ether |
| 7 | Poly (propylene glycol) diglycidyl ether |
| 8 | Glycerol diglycidyl ether |
| 9 | Poly(ethylene glycol) diacrylate |
| 10 | Hexamethylene diacrylate |
| 11 | Neopentyl glycol diacrylate |
| 12 | 1.3-Butanediol diacrylate |
| 13 | 1,6-Hexanediol diacrylate |
| 14 | Bisphenol A ethoxylate diacrylate |
| 15 | Ethylene glycol diacrylate |
| 16 | 1,4-Butanediol diacrylate |
| 17 | Glycerol 1,3-diglycerolate diacrylate |
| 18 | Neopentyl glycol diacrylate |
| 19 | Tetra(ethylene glycol) diacrylate |
| 20 | Poly(propylene glycol) diacrylate |
| 21 | Tri(ethyleneglycol) diacrylate |
| 22 | 1,6-Hexanediol ethoxylate diacrylate |
| 23 | Neopentyl glycol propoxylate (1 PO/OH) diacrylate |

Fig. 2

|  | No Span-80 added | Span-80 added |
|---|---|---|
| p-value of One-way ANOVA | 0.00162 | 0.174 |

| Batch of Amikabeads-Q | Average Diameter (μm) ± 1 S.D (Standard Deviation) | $Q_{max}$ DNA Binding Capacity (μg pDNA bound/mg of beads) |
|---|---|---|
| n=1 | 12 ± 6 | 333.3 |
| n=2 | 15 ± 7 | 277 |
| n=3 | 10 ± 6 | 296 |

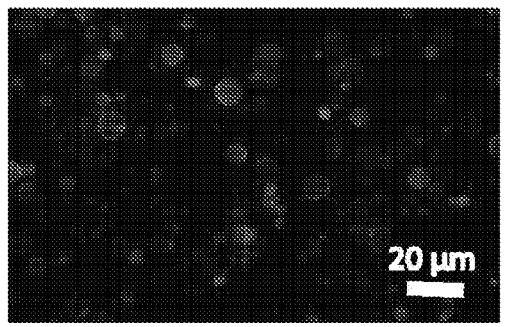
Fig. 10A                Fig. 10B
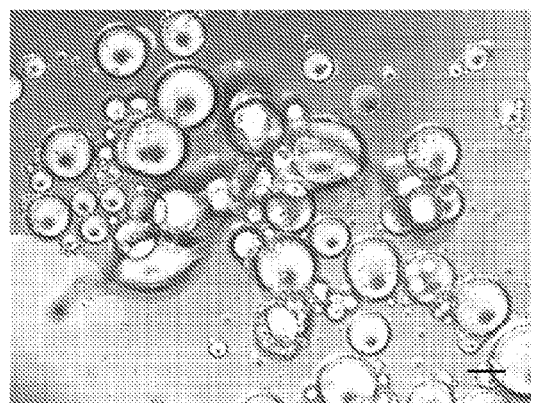
Fig. 11
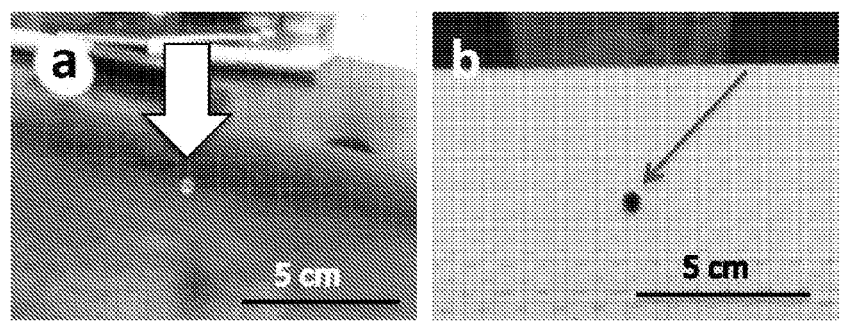
Fig. 12A        Fig. 12B

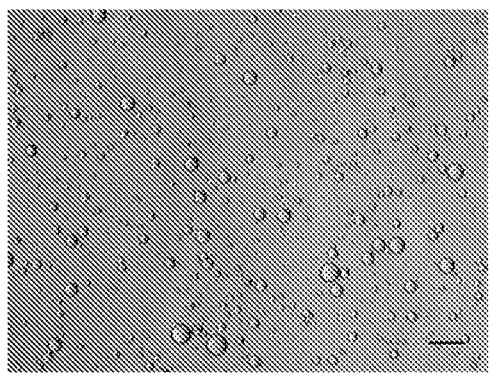 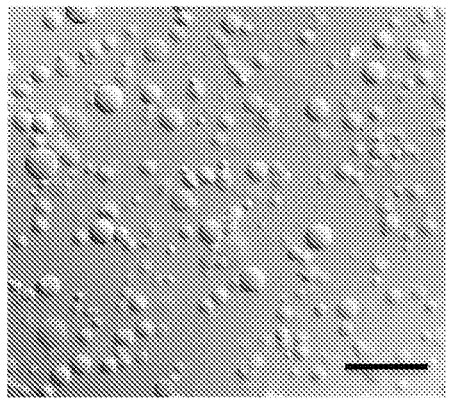
Fig. 16A          Fig. 16B
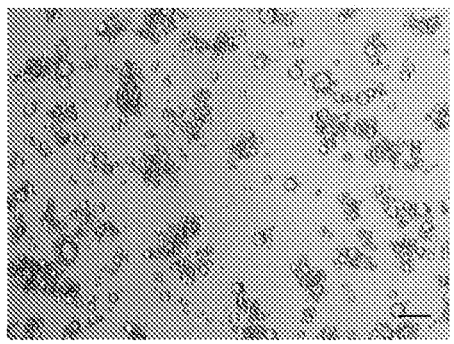 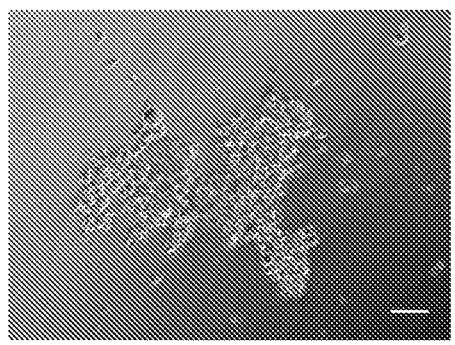
Fig. 16C          Fig. 16D a
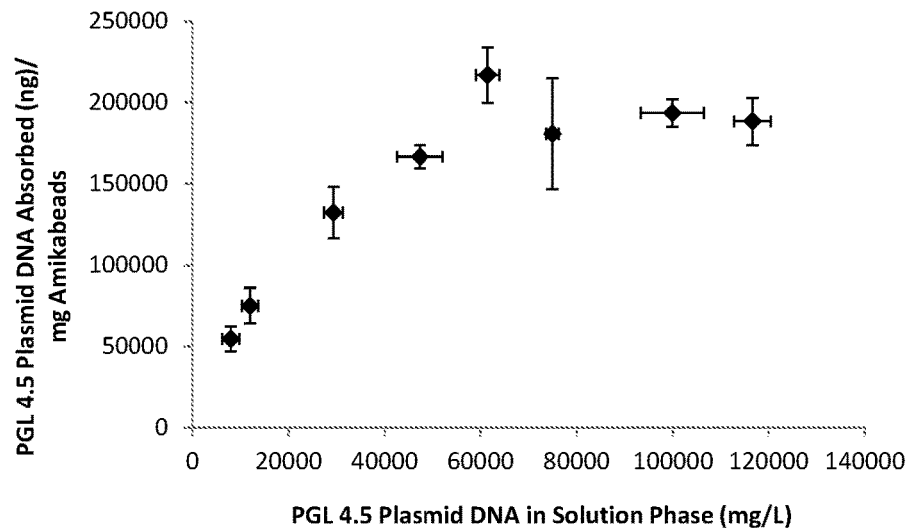
b
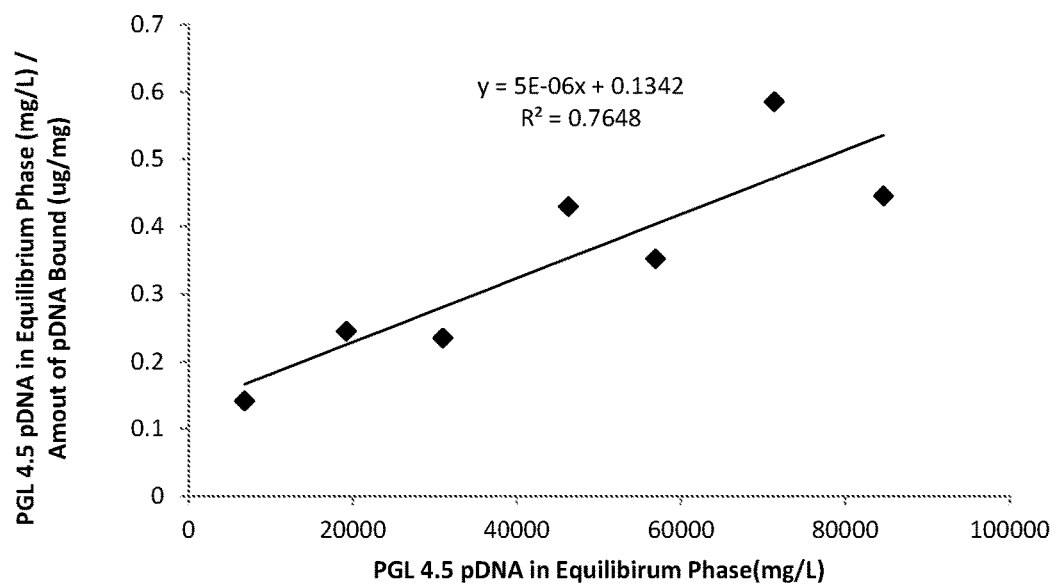
Fig. 23

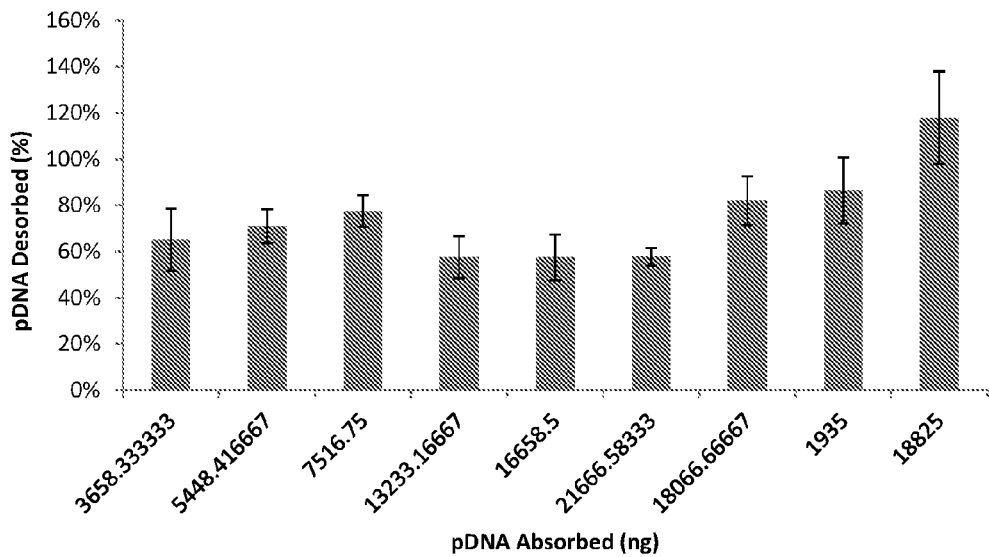
A.
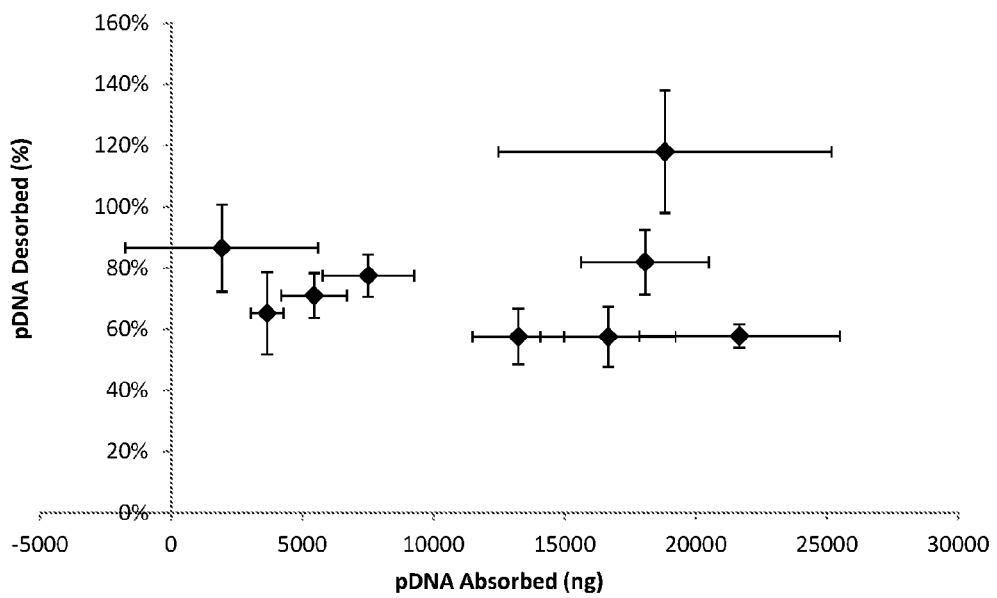
B.
Fig. 24

AMINOGLYCOSIDE HYDROGEL MICROBEADS AND MACROPOROUS GELS WITH CHEMICAL CROSSLINK, METHOD OF PREPARATION AND USE THEREOF

CROSS-REFERENCE TO RELATED APPLICATIONS

This application represents the U.S. National Stage of International Application No. PCT/US2016/017771. filed Feb. 12. 2016. which claims priority to U.S. provisional patent application 62/115,392 filed on Feb. 12, 2015 , the disclosures of which are incorporated by reference herein in their entirety.

FEDERALLY SPONSORED RESEARCH OR DEVELOPMENT

This invention was made with government support under 1067840 awarded by the National Science Foundation. The government has certain rights in the invention.

FIELD OF THE INVENTION

Aminoglycoside hydrogel based microbeads and monoliths with chemical cross-linkings are formed by mixing a polymer with a cross-linking agent. A method of preparing the same, and a use thereof, are also disclosed.

BACKGROUND OF THE INVENTION

Aminoglycoside antibiotics including neomycin, streptomycin, kanamycin, apramycin and paromomycin are known to prevent growth of gram-negative bacteria by inhibiting protein synthesis. The mode of action of aminoglycoside antibiotics involves binding and stabilizing 16s rRNA and complexing with 30S subunit of ribosome. This, in turn, inhibits protein synthesis and causes bactericidal activity. Aminoglycosides possess biocompatible sugar groups as well as multiple amines in the same molecule. Their natural affinity towards nucleic acids, makes them excellent candidates for generating diverse materials in nucleic acid biotechnology.

BRIEF DESCRIPTION OF THE DRAWINGS

The invention will be better understood from a reading of the following detailed description taken in conjunction with the drawings in which like reference designators are used to designate like elements, and in which:

FIG. 1 recites a list of antibiotic aminoglycosides that can be used for preparation of hydrogel microbeads and monoliths;

FIG. 2 recites a of crosslinkers that can be used to generate hydrogel microbeads and monoliths;

FIG. 6($b$) Desorption of plasmid DNA from Amikabeads-P (1 mg) using Tris-Cl buffer with 1 M salt (0.99 M NaCl, 10 mM Tris-Cl, pH 8.5) after 24 hours (diamonds), and Tris-Cl buffer with 1.3 M salt (1.25 M NaCl, 50 mM Tris-Cl, pH 8.5) supplemented with 15% isopropanol (squares) at 25° C.;

FIG. 7 a graphically illustrates Adsorption isotherm of pGL4.5 plasmid DNA on quaternized Amikabeads-Q (Average diameter: 12±6 μm) in (Buffer I) 10 mM, Tris.HCl buffer, pH 8.5, at 25 oC following equilibration for 24 hours. Quaternization of Amikabeads greatly enhanced the plasmid DNA binding capacity compared to Amikabeads-Q ($p<0.001$);

FIG. 10a shows in situ DNA capture using Amikabeads-P from mammalian cells and 500 μg Amikabeads-P (approximate diameter: ~12±4 μm) exposed to 10,000 PC3 prostate cancer cells for 24 hours followed staining with the nucleic acid binding dye, ethidium homodimer-1. Nucleic acids adsorbed to the beads were stained red;

FIG. 10b shows no red fluorescence was observed with ethidium homodimer-1 stained Amikabeads in the absence of bound DNA. Scale bar=20 μm;

FIG. 11 recites an optical image of Amikabeads-P prepared in silicone oil in absence of stabilizing surfactant. Scale bar=100 μm;

FIG. 12a recites an optical image of 0.5 mm model Amikabead-P indicated by an arrow;

FIG. 12b shows reaction with the ninhydrin assay reagent resulted in blue-purple color throughout the Amikabead (red arrow), indicating presence of reactive primary amines;

FIG. 16a shows an optical image Amikabeads-P before loading with (c) 40,000 ng and (d) 280,000 ng of pDNA/mg of beads;

FIG. 16b shows an optical image of Amikabeads-Q before loading with (c) 40,000 ng and (d) 280,000 ng of pDNA/mg of beads;

FIG. 16c shows an optical image Amikabeads-P after loading with (c) 40,000 ng and (d) 280,000 ng of pDNA/mg of beads;

FIG. 16d shows an optical image of Amikabeads-Q after loading with (c) 40,000 ng and (d) 280,000 ng of pDNA/mg of beads;

FIG. 23A depicts pDNA absorbed per 1 mg of doxo-beads against with pDNA in solution phase.

FIG. 23B depicts pDNA in equilibrium phase per amount of pDNA bound to the Amikabeads against with pDNA in equilibrium phase. The inverse of slope shows the maximum pDNA binding capacity for doxo-beads. The maximum binding capacity of PGL 4.5 pDNA for doxo-beads is found out to be 200 mg.

FIG. 24 depicts pDNA desorbed from doxo-beads in percentage against with pDNA absorbed on the surface of beads.

DETAILED DESCRIPTION OF THE PREFERRED EMBODIMENTS

This invention is described in preferred embodiments in the following description with reference to the FIGs, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicants disclose the generation of amikacin antibiotic-derived microbeads, 'Amikabeads', as anion-exchange resins for potential use in pDNA purification as well as in situ capture of DNA from mammalian cells.

Applicants further disclose a new microresin and macroporous monolith based material for plasmid DNA binding and purification, mammalian whole cell genomic DNA extraction and in-vitro cell culture. The monolith and microresins are based on crosslinked aminoglycoside monomer. Aminoglycoside and a diepoxide crosslinker were emulsified into microdroplets and allowed to gel to generate the microbeads for plasmid DNA binding. In addition, the microbeads were then surface conjugated with multiple ligands to improve their plasmid DNA binding capabilities. The aminoglycoside after microbead formation contains multiple units of aminoglycosides rich in primary amines and hydroxyls. These primary amines and hydroxyls can be further conjugated with multiple ligands useful for plasmid DNA binding. Aminoglycoside and crosslinker in organic solvent were used to wet a salt column before crosslinking. After crosslinking, the salt was dissolved away to leave a macroporous column that can be used as monoliths for plasmid DNA binding, 3D cell culture etc.

Figure 4A:
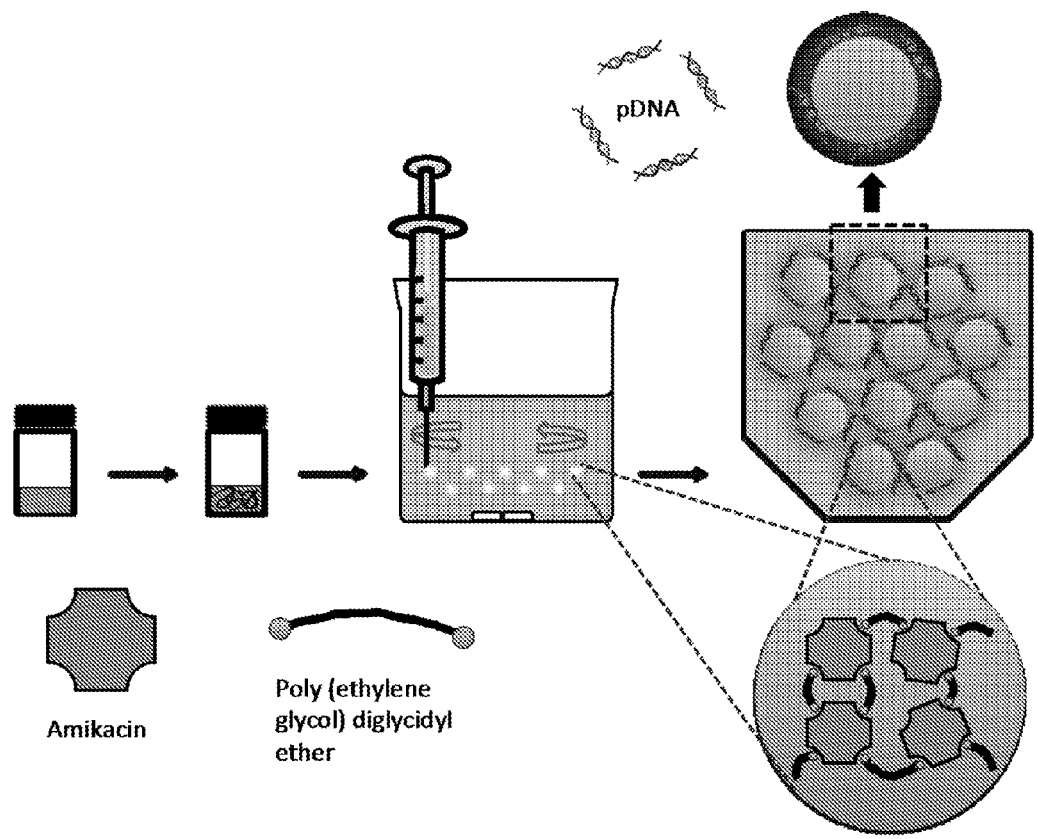
FIGS. 4a and 4b recite schematic overview of Amikabead-P synthesis. In certain embodiments, Amikabeads were prepared by pre-gelling the Amikagel solution for 4 minutes at 70° C. The pre-gelled Amikagel solution was added to mineral oil bath supplemented with 1% Span 80 surfactant and maintained at 65° C.
Figure 4B:
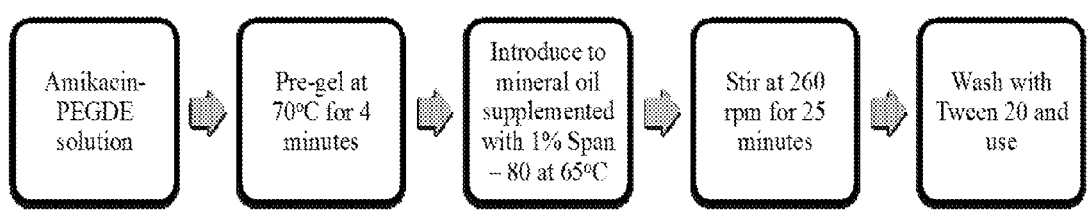

Reaction between amines present in amikacin with the epoxide groups in PEGDE resulted in the formation of a crosslinked hydrogel ('Amikagel') as shown in FIG. 1. Multiple amines in Amikagel, particularly in the form of microbeads, can be exploited for nucleic acid (pDNA) biotechnology. Parental Amikabeads-P were generated using an emulsion polymerization method (FIG. 2a-b); a cross-linking ratio of 1:2 amikacin to PEGDE was used. The amikacin-PEGDE mixture formed a solid hydrogel within ~8 minutes when stirred at 100 rpm at 70° C. Hence, a pre-gelling time of 4 minutes was chosen, following which, the pre-gelled Amikagel solution was introduced into the heated mineral oil phase (65° C., constant stirring at 260 rpm) (FIG. 2). In all cases, mineral oil was supplemented with 1% Span-80 surfactant (w/v) in order to stabilize the water-in-oil microemulsion. Microbeads synthesized in absence of stabilizing surfactant were irregular and non-spherical (FIG. 11). Amikabeads-P formed in mineral oil were separated from the oil phase by centrifugation at 5000g for 10 minutes, following which, the microbeads were extensively washed with nanopure water supplemented with 1% (v/v) Tween 20. Addition of Tween 20 allowed the removal of remaining Span-80 and mineral oil. Tween and Span surfactants are often mixed together in order to generate surfactants of desired Hydrophilic:Lipophilic Balance (HLB) values (Note: An HLB value of more than 10 is necessary in order to ensure surfactant solubility in water). Given the insolubility of Span-80 in water (HLB value of 4.3), Tween-20 (HLB value of 16.3) was added to solubilize and remove any remaining Span-80 and mineral oil 7. The steps used to generate Amikabeads-P are shown in FIG. 4a, b.

Characterization of Amikabeads

Shape and Particle Size of Amikabeads

Figure 4C:
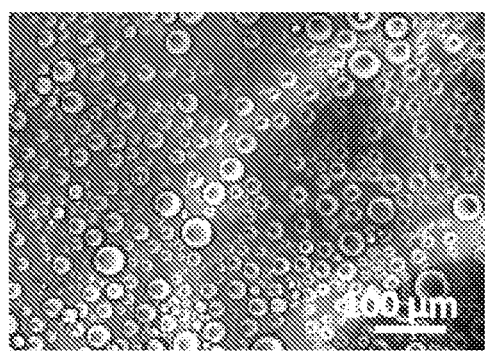
FIG. 4c comprises a phase-contrast image of Amikabeads-P generated after emulsion polymerization of Amikacin-PEGDE in mineral oil-1% Span 80 solution. Scale bar: 100 μm.
Figure 4D:
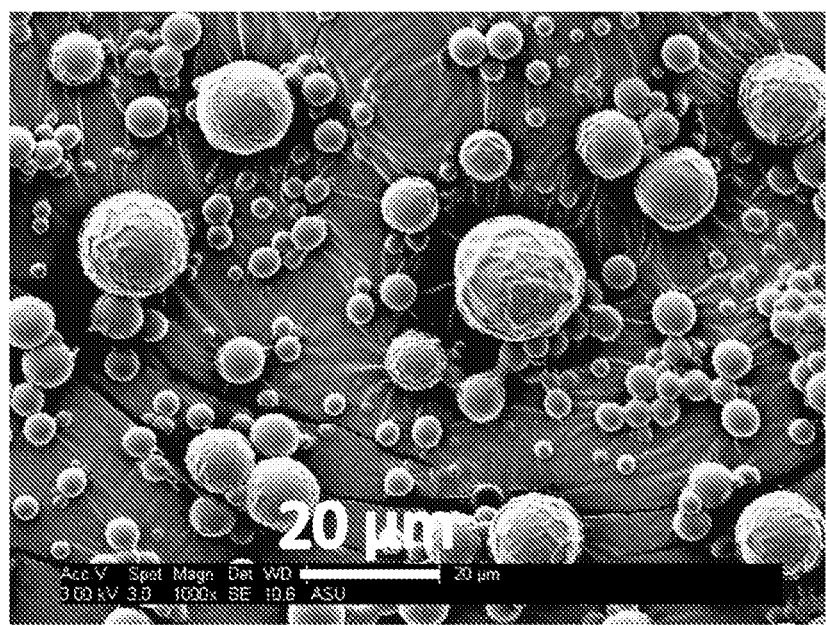
FIG. 4d recites a scanning electron microscopy (SEM) image of Amikabeads indicates spherical particles with an average diameter of ~9±4 μm (calculated over 50 beads). UV radiation can be used as photoinitiator for reactions using acrylates and amines.
Figure 5A:
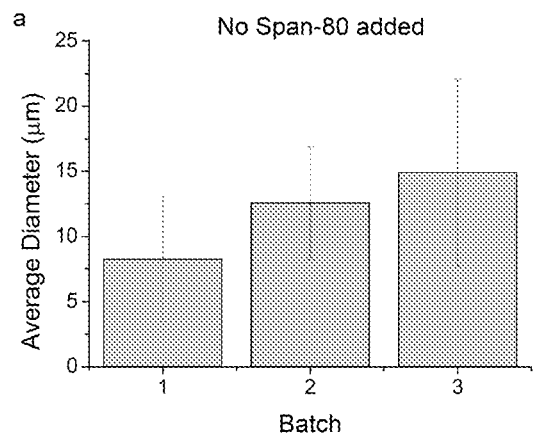
FIG. 5a graphically shows average Amikabead-P diameter±one standard deviation (in microns) of three consecutive batches in absence of additional Span-80. The p-values for the one-way ANOVA test are also shown for n=5 independent experiments.

Amikabeads-P generated using the above emulsion system were found to have spherical morphology and demonstrated minimal aggregation (FIG. 4c). However, it is likely that in a chromatographic setting of a tightly packed column, Amikabeads will be in close contact with each other. Amikabeads-P were sputter-coated with 8 nm thick coating of Au—Pt in order to visualize them using scanning electron microscopy (SEM). As shown in FIG. 4d, Amikagel-P microbeads had a predominantly spherical shape with smooth as well as rough surface morphology, which is similar to other hydrogel microbeads described previously 8. The average diameter of Amikabeads-P was ~9±4 microns (FIG. 4d), and was dependent on the number of times the mixture of mineral oil and span 80 was used in serial batches. Upon repeated usage of mineral oil and span 80, the diameters of Amikabeads demonstrated a modest increase ($p<0.01$, one-way ANOVA) (FIG. 5a).

Figure 5B:
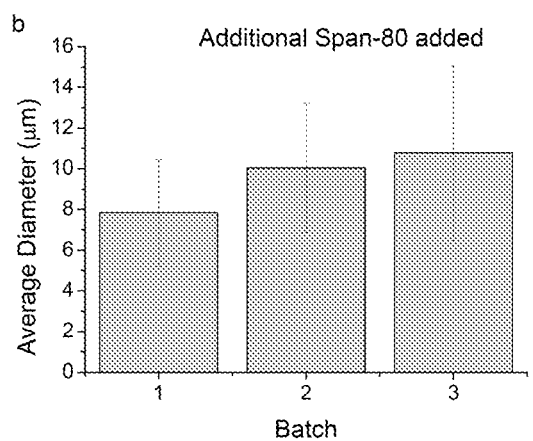
FIG. 5b graphically shows average Amikabead-P diameter±one standard deviation (in microns) of three consecutive batches in presence of Span-80. The p-values for the one-way ANOVA test are also shown for n=5 independent experiments.

In certain embodiments, Applicants introduce additional fresh Span-80 after every batch of Amikabead synthesis to limit the batch-to-batch variation in the bead size. This supplementation accounts for any losses in Span-80 by thermal degradation during the preparation of each batch. As seen in FIG. 5b, the diameter of Amikabeads-P did not change significantly with addition of 400 mgs of fresh Span-80 after each batch of preparation. An observed p-value of 0.174 indicated that it is not possible to reject the null hypothesis that particle diameters in all three consecutive batches are the same in FIG. 5b (p-value threshold of 0.05 for statistical significance). Thus, addition of Span-80 indeed reduced the batch-to-batch variation in particle diameter/size. Following this observation, Applicants were able to mix different batches in order to obtain high amounts of Amikabeads-P for subsequent investigations.

Amikabeads-P demonstrated a swelling ratio of approximately 1.74±0.2 (or 174%). This is similar to commercially available anion-exchange resins, which demonstrate swelling ratios of up to 200%. For example, polystyrene-divinylbenzene (PS-DVB) beads containing quaternary ammonium groups used as strong anion exchange resins demonstrated a swelling ratio of 1.7, which is very similar to that of Amikabeads.

Amine Content of Amikabeads

The presence of accessible amine moieties is critical for the use of Amikabeads in anion-exchange applications. Furthermore, presence of reactive amines allows for subsequent conjugation chemistries if required. The reaction of ninhydrin reagent with reactive (primary and secondary amines) results in colorimetric changes; a bluish-purple color can be observed upon reaction with primary amines 11. Reaction of a 0.5 mm model Amikabead with 100 μL of ninhydrin reagent at 70° C. for ten minutes resulted in the formation of intense bluish-purple color throughout the bead (FIG. 12b). The amine content of lyophilized Amikabeads-P was estimated to be 1.8±0.3 μmoles of amine per milligram of Amikabeads.

pDNA Binding to Amikabeads-P

The binding of pDNA to Amikabeads-P was determined using batch adsorption assays, in order to determine the potential use of these microbeads as anion-exchange resins; the pGL4.5 luciferase pDNA was used as a model plasmid in all batch binding experiments. The pGL4.5 plasmid codes for luciferase reporter protein, which is commonly used for analyzing the transfection efficacy of various non-viral vectors 12. The Langmuir adsorption isotherm was used to fit the experimental data and obtain parameters including the maximum binding capacity (Qmax) and equilibrium binding constant (K). Tables 1A and 1B show the different parameters generated by fitting the experimental adsorption isotherm data to a Langmuir isotherm; the Langmuir adsorption equation was converted to its linear form in order to determine the Qmax value. The average (n=3) maximum adsorption capacity (Qmax) calculated by fitting the adsorption isotherm of the Amikagel-P microbeads was approximately 44.5 μg pDNA/mg of Amikabeads-P with an equilibrium constant K of 0.04-0.06 L/mg at an equilibrium pDNA concentration (solution phase) of 300-400 mg/L. Further increasing the concentration of pDNA in the solution phase did not result in any increase in the amount of DNA adsorbed on Amikabeads-P, indicating saturation (FIG. 5a, diamonds).

TABLE 1A recites adsorption of plasmid DNA to Amikabeads-P in presence of 10 mM Tris-Cl buffer (pH 8.5) (Buffer I)

TABLE 1A

| ID | Average bead size (μm) | $Q_{max}$ (μg/mg) | K (L/mg) | R-square |
|---|---|---|---|---|
| 1 | 10 ± 3 | 56.0 | 0.01 | 0.97 |
| 2 | 11 ± 5 | 46.4 | 0.02 | 0.88 |
| 3 | 12 ± 4 | 31.5 | 0.05 | 0.96 | pDNA binding to Amikabeads-P was significantly reduced in presence of 0.3 M (buffer II) and 0.6 M salt (buffer III). TABLE 1B recites adsorption of plasmid DNA to Amikabeads-P in presence of 300 mM Tris-Cl -NaCl buffer (pH 8.5) (Buffer II) and 600 mM Tris-Cl—NaCl buffer (pH 8.5) (Buffer III).

Figure 6A:
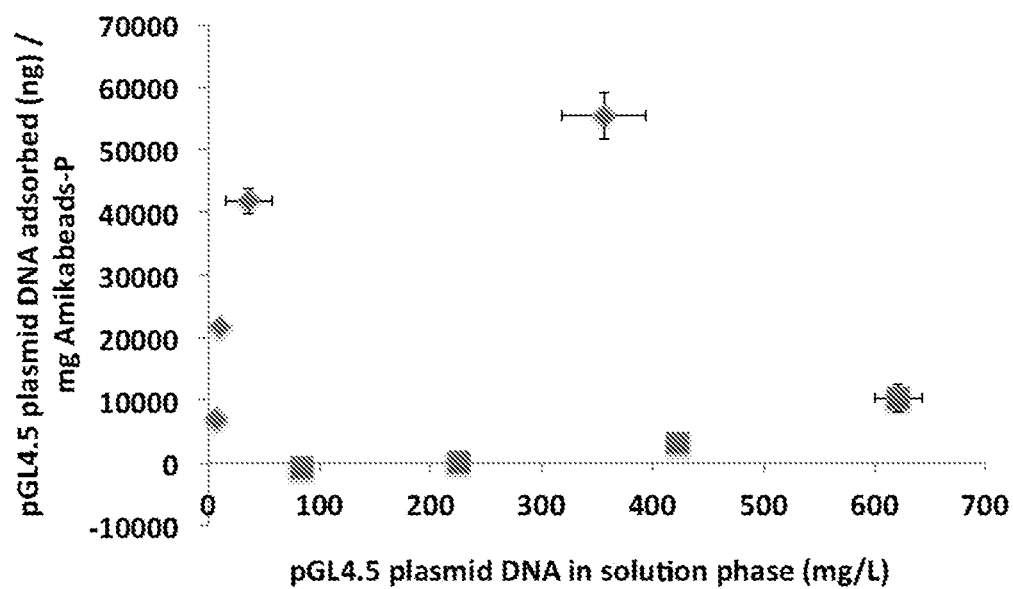
FIG. 6($a$) graphically illustrates Isotherm of pGL4.5 plasmid DNA adsorption on Amikabeads-P of diameter 11±4 μm in presence of (Buffer I) 10 mM, Tris.HCl buffer, pH 8.5, at 25° C. for 24 hours (diamonds). Maximal adsorption ($Q_{max}$) is 44.5 μg of plasmid DNA/mg of Amikabeads-P (n=3) (diamonds). Effect of (Buffer II) 0.3 M salt on plasmid DNA adsorption on Amikabeads of average diameter 12±4 μm (squares). Reduced pDNA binding can be observed, indicating that electrostatic interactions drive adsorption.

As expected, higher salt concentrations screen electrostatic charges and obviate interactions between negatively charged DNA molecules and the positively charged Amikabeads-P. The saturation amount of pDNA on Amikabeads-P was not calculated under these elevated salt concentrations, since the adsorption isotherm was found to in the linear range, even for very high pDNA concentrations in the solution phase (FIG. 6a; squares).

Figure 6B:
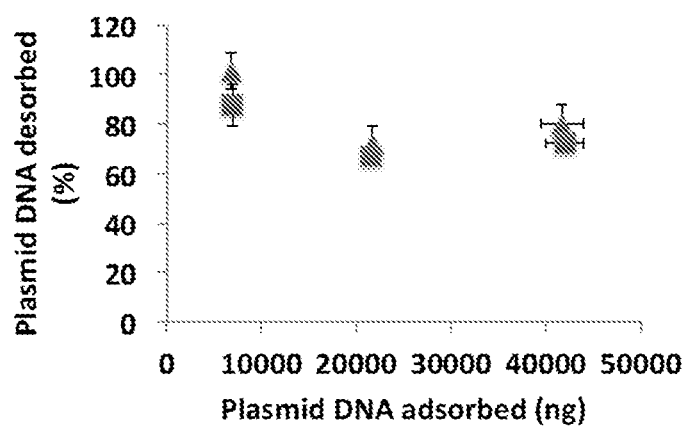

Recovery of pDNA from Amikagels-P bound under low salt conditions (i.e. 10 mM Tris-Cl, pH 8.5) was investigated using Tris-Cl buffer with 1 M salt (0.99 M NaCl and 10 mM Tris-Cl, pH 8.5) and Tris-Cl buffer with an organic modifier (50 mM Tris-Cl and 1.25 M NaCl, with 15% isopropanol, pH 8.5). Approximately 70-100% of originally adsorbed pDNA was desorbed when a salt concentration of 1M was used. No improvement in desorption was noticed when a buffer with higher salt concentration and isopropanol was used (FIG. 6b), indicating that hydrophobic modifiers did not help recovery from Amikabeads-P. Higher percentages of desorption was observed when lesser amounts of pDNA were adsorbed onto the beads, indicating marginal losses in recovery at higher loadings (FIG. 6b).

Quaternization of Amikagel-P Beads Enhances pDNA Binding

Figure 13A:
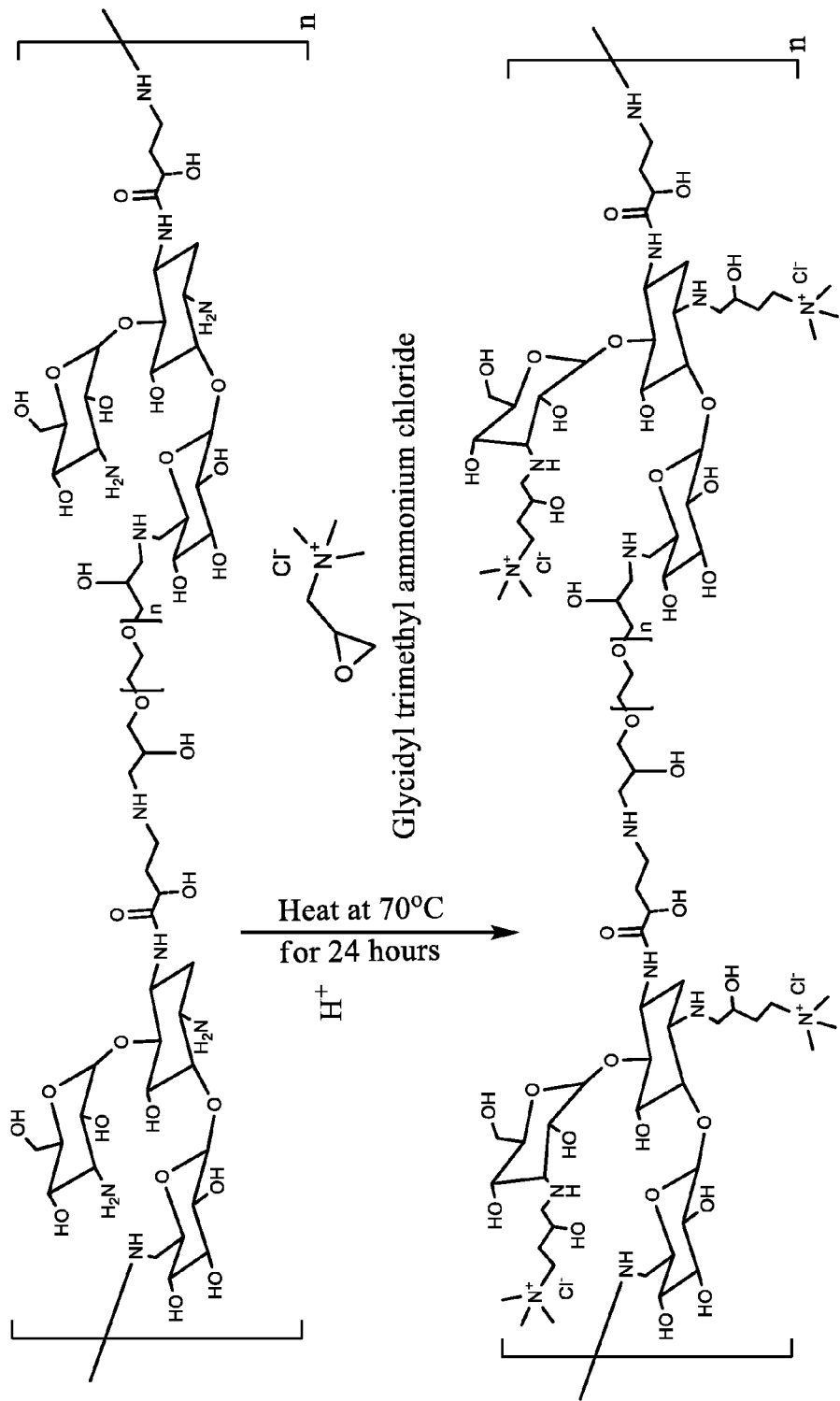
FIG. 13a shows Amikabeads-P reacted with excess glycidyl trimethyl ammonium chloride (GTMAC) at 70° C. for 24 hours to generate quaternized Amikabeads-Q.
Figure 13B:
FIG. 13b. shows a Ninhydrin test on ~1 mg unmodified Amikabeads-P (left) and quaternized Amikabeads-Q (right). Formation of blue-purple color indicates presence of reactive (primary) amines.
Figure 13C:
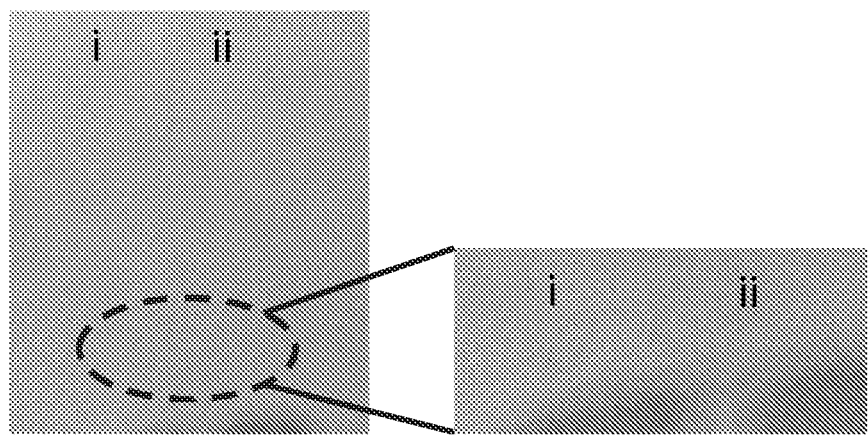
FIG. 13c shows a fluorescein binding assay after incubating (i) Amikabeads-P and (ii) Amikabeads-Q with 200 μL of 50 mg/mL of fluorescein sodium in 1% (v/v) NaOH solution (pH>12) in nanopure water for 10 minutes, followed by extensive washing. Formation of intense red color in the pellet indicates increased fluorescein retention by Amikabeads-Q, and thus, presence of quaternary amine groups. Lesser retention of fluorescein was observed in the case of the parental Amikabeads-P.

Amikacin has 4 primary amines, one secondary amine and 8 hydroxyl groups. Quaternization of amine groups can help increase the content of positive charges in the microbeads. This in turn, was anticipated to result in enhanced pDNA binding efficacy. The amines on the microbeads were therefore modified to quaternary amines using glycidyl trimethyl ammonium chloride (GTMAC), at neutral or acidic pH, only the amines of the amikacin react with the epoxide group of GTMAC as an addition reaction 13 (FIG. 13(a)). Formation of quaternary amines on Amikabeads was verified using both, the ninhydrin assay as well as the fluorescein-binding assay. Ninhydrin reagent reacts with primary amines resulting in the formation of a blue-purple colored product. However, as expected, quaternized Amikabeads-Q did not demonstrate a blue color unlike unmodified Amikabeads-P (FIG. 13(b)). The fluorescein-binding assay was also able ascertain quaternization in Amikabeads-Q; in presence of 1% (v/v) NaOH (pH>12), the primary amines present on amikacin are no longer positively charged, whereas the quaternary amines on the quaternized beads retain the permanent positive charge. Hence, the negatively charged fluorescein can interact with and bind the quaternary ammonium moieties in Amikabeads-Q, but not the primary amines in Amikabeads-P (FIG. 13(c)).

Figure 14A:
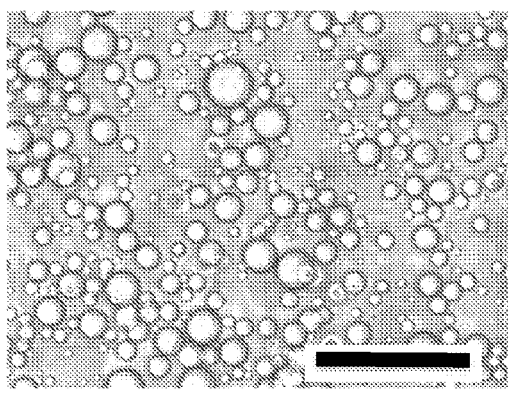
FIG. 14a shows representative images of Amikabeads ~11±4 μm in diameter before quaternization using glycidyl trimethyl ammonium chloride (GTMAC). Scale bar=100 μm.
Figure 14B:
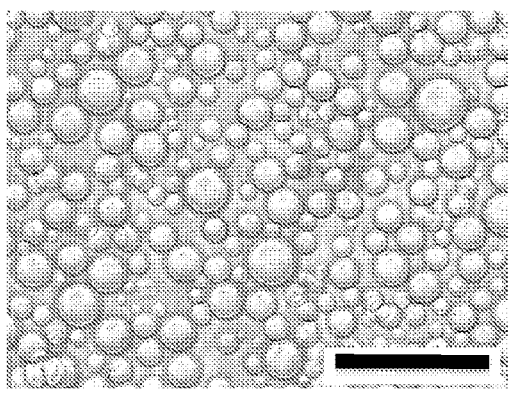
FIG. 14b shows representative images of Amikabeads ~11±4 μm in diameter after quaternization using glycidyl trimethyl ammonium chloride (GTMAC). Scale bar=100 μm.
Figure 14C:
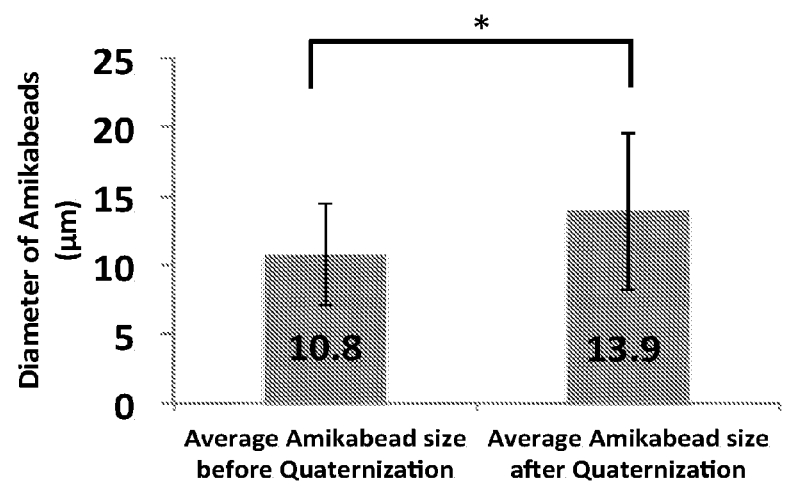
FIG. 14c graphically shows a diameter of Amikabeads-P and -Q. Quaternization did not change the spherical shape, but modestly increased the average diameter of Amikabeads by ~1.3 fold (* indicates p<0.005)
Figure 15:
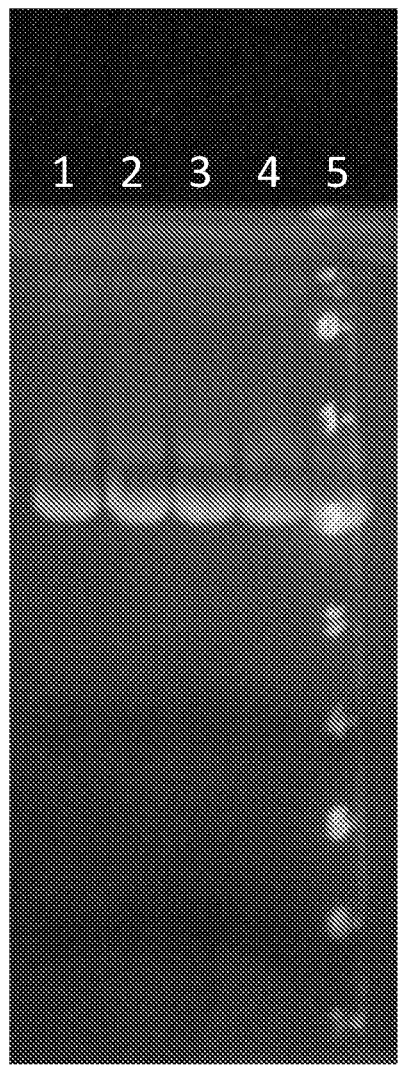
FIG. 15 shows Agarose gel electrophoresis (AGE; 1% agarose gel) of desorbed plasmid DNA recovered from unmodified parental (P) and quaternized (Q) Amikabeads. Vertical Lanes 1 and 2—Plasmid DNA desorbed from quaternized Amikabeads-Q (n=2). Lanes 3 and 4—Plasmid DNA desorbed from unmodified Amikabeads-P (n=2). Lane 5—Stock solution of plasmid DNA used in the binding studies. No visible differences can be seen between the desorbed pDNA and the stock pDNA, indicating the pDNA integrity is maintained upon binding and desorption from Amikabeads P and Q.

Adsorption experiments indicated that Amikabeads-Q demonstrated significantly higher (p<0.001) pDNA loading capacities than Amikabeads-P (FIG. 5a-b). Average Qmax values, determined after n=3 independent experiments, were approximately 300 µg pDNA/mg of Amikabeads-Q at an equilibrium pDNA concentration of 150-200 mg/L. This pDNA loading was approximately 30% of the weight of the Amikabeads-Q and is almost 7-fold higher than that on Amikabeads-P. Interestingly, Amikabeads-Q demonstrated a slightly higher average diameter than Amikabeads-P (10.8 microns for Amikabeads-P and 13.9 microns for Amikabeads-Q; FIG. 14). This increase in average diameter of Amikabeads-Q could be due to repulsion between the quaternized charges, and may have a minimal contribution to the observed increase in pDNA binding capacity of Amikabeads-Q by increased surface area (~1.66 fold increase over Amikabeads-P).

The static binding capacities of commercially available resins range from 1 to 10 mg of pDNA/mL of resin slurry. Gigaporous rigid ceramic quaternary amine containing HyperD-Q polymerized hydrogel resins and quaternized polyethyleneimine-containing porous resins (POROS HQ resins) possess among the highest static binding capacities at ~10 mg of pDNA/mL of resin slurry. Static pDNA binding capacities of Amikabeads-Q and Amikabeads-P were estimated to be ~6 mg of pDNA/mL of resin slurry and ~1.2 mg of pDNA/mL of resin slurry, respectively, which is comparable to that of several commercially available resins. As described in the methods section, the static binding capacity of Amikabeads was estimated by extrapolating the pDNA binding on 1 mg or 50 µL of Amikabeads-Q to 1 mL.

Desorption of pDNA from Amikabeads-Q

Figures 7A, 7B:
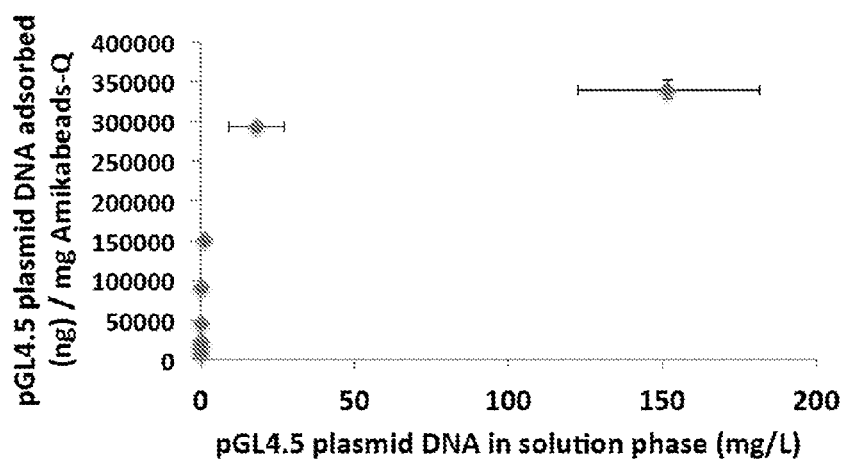
FIG. 7b recites $Q_{max}$ calculated for three independent adsorption experiments in 10 mM, Tris.HCl buffer, pH 8.5, at 25° C. Average $Q_{max}$ calculated for Amikabeads-Q was ~300 μg of plasmid DNA/mg of Amikabeads-Q.
Figure 7C:
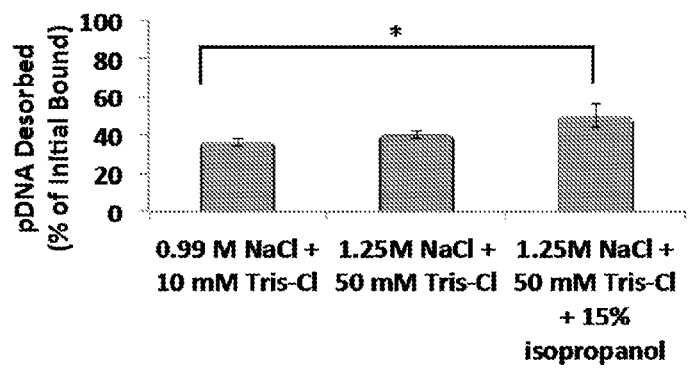
FIG. 7c graphically shows the percentage of bound pDNA desorbed with Tris-Cl buffer with 1 M salt (0.99 M NaCl, 10 mM Tris-Cl, pH 8.5), Tris-Cl buffer with 1.3 M salt (1.25 M NaCl, 50 mM Tris-Cl, pH 8.5) and Tris-Cl buffer with 1.3 M salt (1.25 M NaCl, 50 mM Tris-Cl, pH 8.5) supplemented with 15% isopropanol is shown. Significantly higher desorption of pDNA was recorded when isopropanol was used in the eluent ($p<0.05$*, Students' t-test)
Figure 7D:
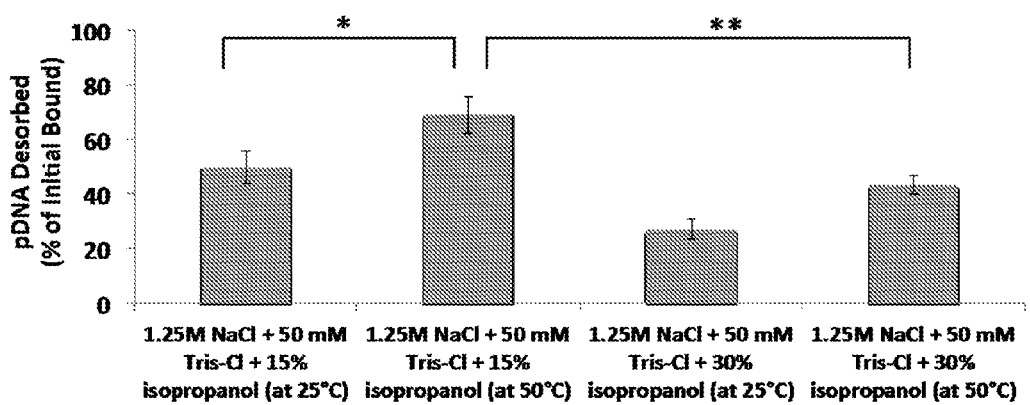
FIG. 7d graphically shows desorption of pDNA from Amikabeads-Q at elevated temperature (50 oC) and higher percentage of isopropanol (30%). Increasing the temperature from 25 oC to 50 oC significantly improved the amount of pDNA desorbed ($p<0.05$*, Students' t-test) while increasing the percentage isopropanol in the buffer from 15% to 30% had the opposite effect ($p<0.001$**, Students' t-test)

Up to 40% of bound pDNA was desorbed from Amikabeads-Q when eluted with Tris-Cl buffer with 1M salt (0.99 M NaCl and 10 mM Tris-Cl, pH 8.5) at 25° C. (FIG. 7c), which was significantly less in percentage than desorption from Amikabeads-P. Thus, while Amikabeads-Q were able to bind higher quantities of pDNA, complete recovery of the beads was not possible using 1 M salt. Improved recovery was seen when Tris-Cl buffer with 15% isopropanol (1.25 M NaCl and 50 mM Tris-Cl, pH 8.5) was employed for desorption at 25° C. (FIG. 7c). Use of 1.25M NaCl did not enhance desorption of pDNA from Amikabeads-Q in absence of isopropanol (FIG. 7c), indicating that the hydrophobic modifier was important for pDNA recovery from Amikabeads-Q. It is known that addition of small organic molecules to desorption buffers reduces the polarity of the solution, which can facilitate desorption of molecules from resins. It is likely that in addition to the anion-exchange character of the quaternary ammonium groups, the presence of three methyl groups in a GTMAC molecule, imparts a modest, but collective hydrophobic character to Amikabeads-Q. As a result, isopropanol may act as a hydrophobic modifier, resulting in an increase in desorption of pDNA from Amikabeads-Q. Interestingly, this opens up the possibility of screening a variety of different small-molecule organic modifiers for enhancing pDNA recovery from these resins, which clearly have the advantage of high binding capacities.

pDNA desorption was greatly increased when the temperature was raised from 25° C. to 50° C. (p<0.001) (FIG. 7d) in presence of 15% isopropanol; a recovery of 70±6% of initially adsorbed pDNA was obtained at 50° C. Higher temperatures are known to facilitate increased desorption of pDNA from chromatographic columns 17. Interestingly, increasing the isopropanol percentage beyond 15% did not improve recovery but rather decreased the pDNA content desorbed into the solution phase (p<0.05) (FIG. 7d).

The quality of the recovered pDNA from the unmodified Amikabeads-P and the quaternized Amikabeads-Q was determined by running it on a 1% agarose gel. The desorbed pDNA recovered by the addition of salt was of the same integrity as that of the pDNA that was loaded on the resin, indicating that Amikabeads did not induce any visible or gross damage to pDNA.

Comparison of pDNA Adsorption on and Desorption from Amikabeads-P vs. Amikabeads-Q As described hereinabove, Amikabeads-Q demonstrated significantly higher (p<0.001) pDNA loading capacities than Amikabeads-P (FIG. 7a-b) likely due to the higher positive charge of quaternary amines. It is well known that quaternary amine groups (present in Amikabeads-Q) are more positively charged and hydrophilic than primary amines (present in Amikabeads-P). It has been reported that methyl groups on a tetramethylammonium ion were found to promote hydrophilicity rather than hydrophobicity. However, the range for this effect was limited to 0-0.08 mole fraction of the solute. Presence of multiple copies of methyl groups from GTMAC on Amikabeads-Q is likely to impart these materials with a modest hydrophobic character, which is likely absent in Amikabeads-P. However, this hydrophobic character will relatively be modest in comparison to its high hydrophilicity.

It has been reported that higher pDNA desorption from a substrate modified with tetraethyl quaternary ammonium groups in presence of lower amount of isopropanol (~20%), when compared to higher isopropanol amounts (~40%). It has been further suggested that the existence of a threshold alcohol percentage up to which the ability of the alcohol to overcome hydrophobic interactions is greater than the overall increase in the solution dielectric constant. This overcoming of hydrophobic interactions, in turn, allows for increased desorption of an adsorbed molecule from the surface. Once this threshold is crossed, it is thought that the decrease in dielectric constant can help electrostatic interactions dominate, which actually can result in lower desorption of pDNA from the adsorbent. Similar trends can be observed for pDNA desorption from Amikabeads-Q (FIG. 7d). Addition of ~15% isopropanol (v/v) sufficiently increases the hydrophobic character of the solvent causing desorption of pDNA from the surface. Use of 30% isopropanol, however, can significantly modify the dielectric constant such that electrostatic interactions can dominate, resulting in lower pDNA desorption from Amikabeads-Q. Absence of such hydrophobic interactions in Amikabeads-P could be the reason behind no improvement in desorption after addition of organic modifier.

Visualization of Amikabeads before and after pDNA Binding

Confocal fluorescence microscopy was employed in order to visualize the localization of pDNA on the Amikabeads upon binding. As shown in FIG. 8b, pDNA was predominantly found to adsorb on the surface of both, Amikabeads-P and -Q. BET analysis indicated that Amikabeads-P possessed a surface area of approximately 2.0 m2/g and a pore size of 4.0 nm. This pore size is consistent with that of several existing ion-exchange resins, but indicates challenges that may be associated with pDNA transport and penetration into the beads, given the larger size (70-100 nm) of super-coiled pDNA 22. These results can explain the observation that pDNA binding is primarily observed on the surface of Amikabeads.

Figure 8A:
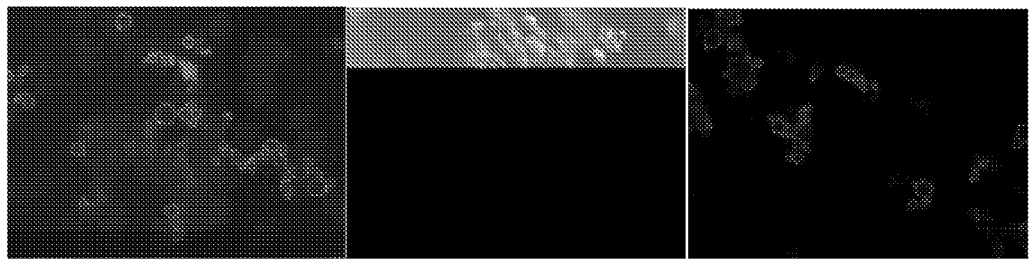
FIG. 8a comprises Confocal microscopy of pDNA loading on Amikabeads-P (average diameter: ~9±4 μm)
Figure 8B:
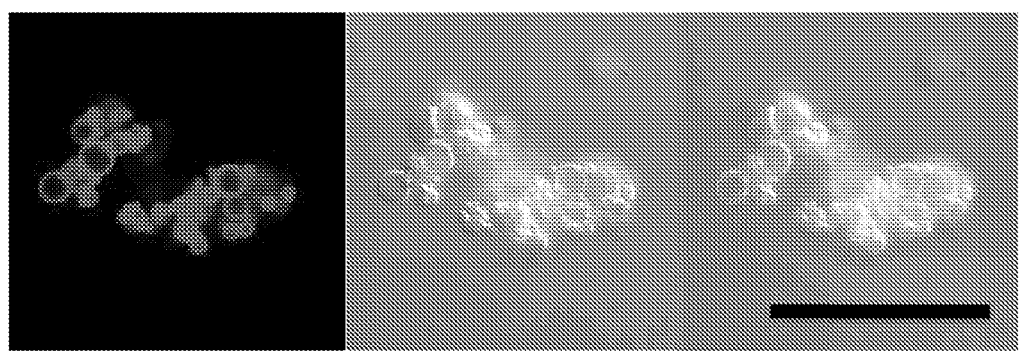
FIG. 8b comprises Confocal microscopy of pDNA loading on Amikabeads-Q (average diameter: ~14±6 μm) is shown. Amikabeads-P and Q (1 mg each) were incubated with 40,000 ng and 200,000 ng of pDNA respectively, in 10 mM Tris-Cl buffer, pH 8.5 at 25 oC for 24 hours. Following washes, the beads were stained with 2 μM ethidium homodimer-1 for 20 minutes prior to imaging. Fluorescence of ethidium homodimer-1 was visualized using an excitation of 528 nm and emission of 617 nm (red color). Plasmid DNA adsorbed on the surface of both, Amikabeads-P and Q, with minimal penetration into the beads. Amikabead clusters were observed after addition of plasmid DNA, possibly due to the bridging.
Figure 8C:
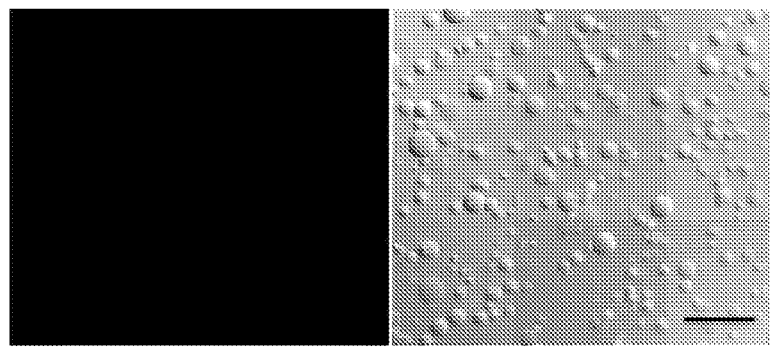
FIG. 8c comprises Confocal microscopy of pDNA loading on Amikabeads not treated with pDNA did not demonstrate ethidium homodimer-1 fluorescence and clustering. A representative image of Amikabeads-Q is shown. Scale bar=100 μm in all cases.
Figure 16E:
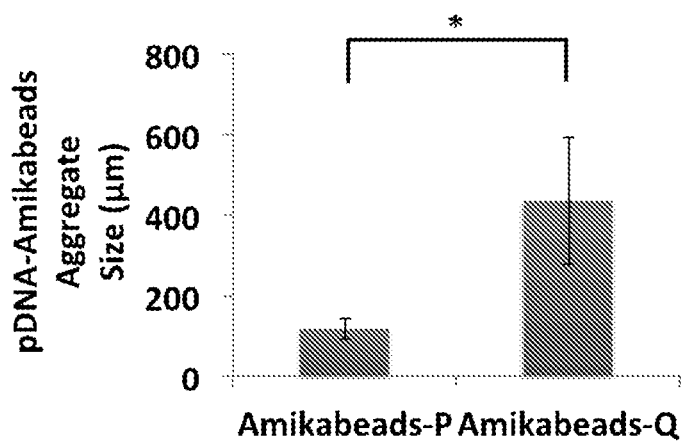
FIG. 16e graphically compares average aggregate sizes of Amikabeads P and Q after loading with pDNA. pDNA-Amikabeads-Q aggregates were significantly bigger than pDNA-Amikabeads-P aggregates (*p<0.001, Students' t-test). Optical images of (f) Amikabeads-P and (g) Amikabeads-Q after desorption with Tris-Cl buffer with 1 M salt (10 mM Tris-Cl, 990 mM NaCl, pH 8.5) and Tris-Cl buffer with 1.3 M salt (50 mM Tris-Cl, 1.25 M NaCl, pH 8.5) respectively. Scale bar=100 μm.
Figure 16F:
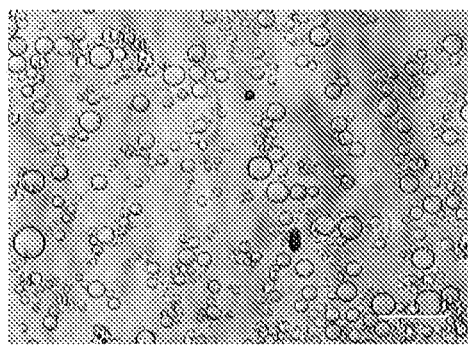
FIG. 16f recites an optical image of Amikabeads-P after desorption with Tris-Cl buffer with 1 M salt (10 mM Tris-Cl, 990 mM NaCl, pH 8.5) and Tris-Cl buffer with 1.3 M salt (50 mM Tris-Cl, 1.25 M NaCl, pH 8.5) respectively. Scale bar=100 μm.
Figure 16G:
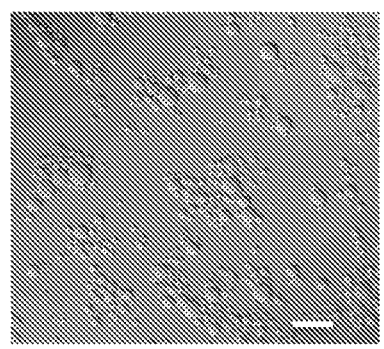
FIG. 16g recites an optical image of Amikabeads-Q after desorption with Tris-Cl buffer with 1 M salt (10 mM Tris-Cl, 990 mM NaCl, pH 8.5) and Tris-Cl buffer with 1.3 M salt (50 mM Tris-Cl, 1.25 M NaCl, pH 8.5) respectively. Scale bar=100 μm.

Following binding of pDNA, Amikabeads-P and Q were found to aggregate, likely due to bridging of the biomacromolecule and the beads (FIG. 8a-b). Neither Amikabeads-P, nor Amikabeads-Q, were found to aggregate in absence of pDNA loading (FIG. 4c, FIG. 16a-b). The average aggregate size of pDNA with Amikabeads-Q was significantly higher than that of Amikabeads-P (p<0.001, Students' t-test; FIG. 16). It is likely that higher positive charge on the Amikabeads-Q allows the formation of bigger aggregates upon pDNA binding, compared to those seen in case of Amikabeads-P. It was noticed that the aggregate size decreased after pDNA desorption. As shown in (FIG. 16f-g), aggregate sizes of both Amikabeads-P and Q decreased after desorption. However, Amikabeads-Q showed lower pDNA desorption with 1 M salt than Amikabeads-P (~40% for Amikabeads-Q vs. ~75% for Amikabeads-P). It is likely that the higher size of aggregates in Amikabeads-Q could have played a role in this lower percent desorption.

Figures 17A, 17B, 17C:
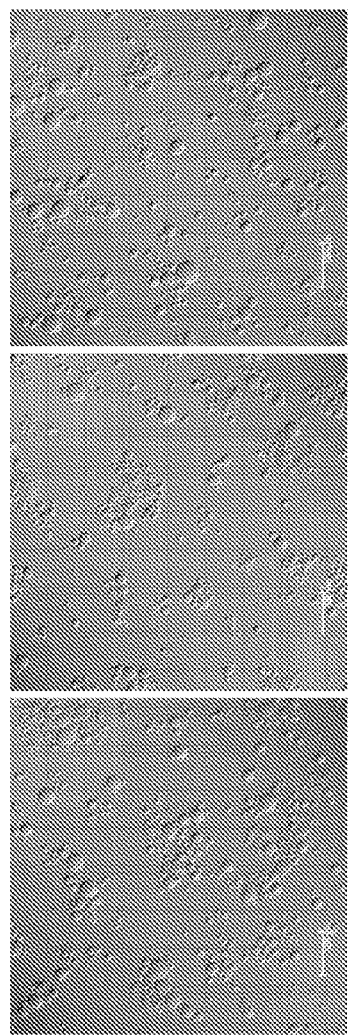
FIG. 17a comprises a phase contrast image (10× zoom) of Amikabeads-Q loaded with 280,000 ng of pDNA/mg of beads treated with Tris-Cl buffer with 1.3 M salt (50 mM Tris-Cl, 1.25 M NaCl, pH 8.5)
FIG. 17b comprises a phase contrast image (10× zoom) of Amikabeads-Q loaded with 280,000 ng of pDNA/mg of beads treated with Tris-Cl buffer with 1.3 M salt (50 mM Tris-Cl, 1.25 M NaCl, pH 8.5) supplemented with 15% isopropanol in absence.
FIG. 17c comprises a phase contrast image (10× zoom) of Amikabeads-Q loaded with 280,000 ng of pDNA/mg of beads treated with Tris-Cl buffer with 1.3 M salt (50 mM Tris-Cl, 1.25 M NaCl, pH 8.5) after elevated temperature (50° C.) for 36 hours.
Figure 17D:
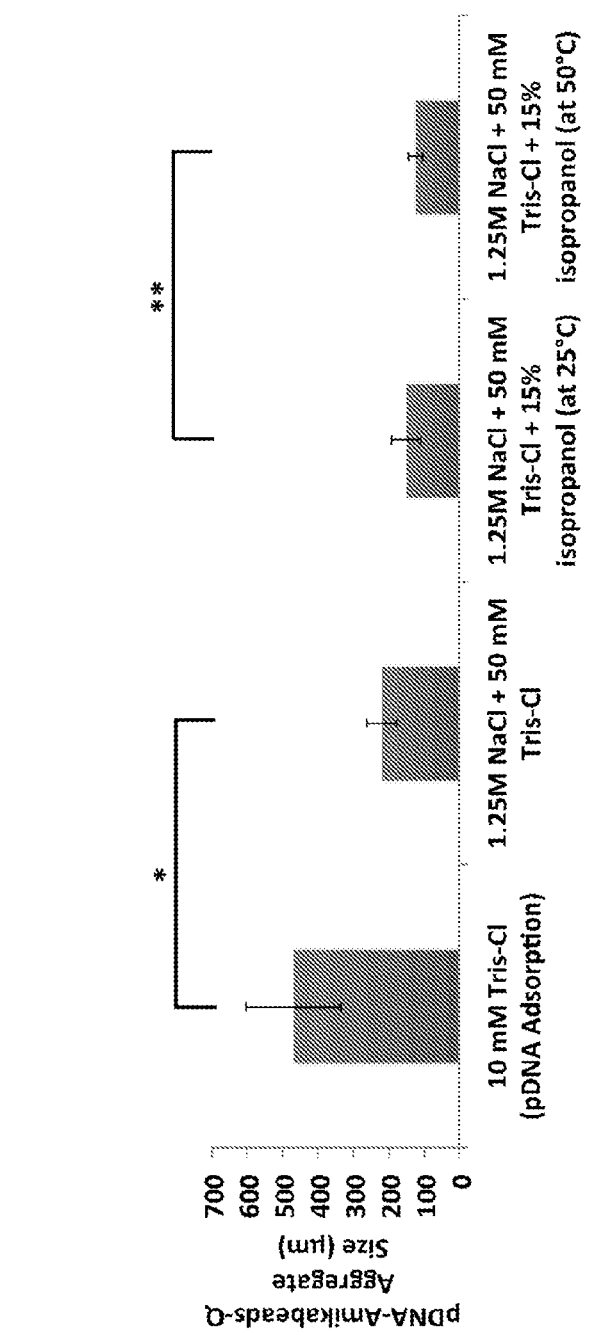
FIG. 17d graphically shows average aggregate size of pDNA-Amikabeads-Q measured before and after treatment with different elution media. Average sizes of aggregates decreased following pDNA desorption (*p<0.001). Equilibration with 15% isopropanol at elevated temperatures (50° C.) significantly decreased the aggregate size (**p<0.05), which was consistent with highest amounts of pDNA desorption seen under these elution conditions.
Figure 17E:
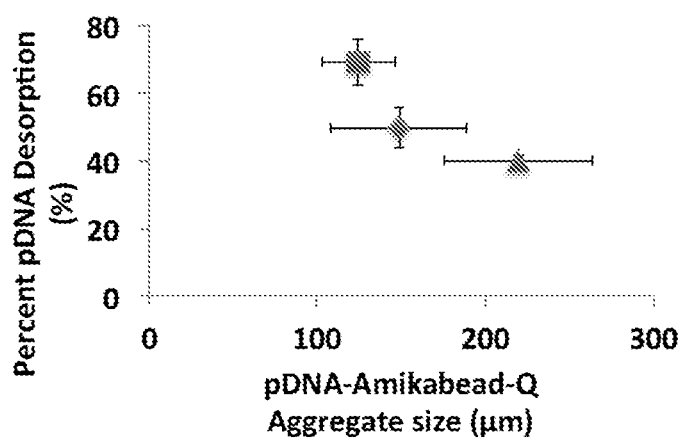
FIG. 17e graphically shows pDNA-Amikabead-Q aggregate size decreased with increasing desorption of the biomacromolecule from the bead surface using different desorption buffers. (Square)—Tris-Cl buffer with 1.3 M salt (50 mM Tris-Cl, 1.25 M NaCl, pH 8.5) (Diamond)—Tris-Cl buffer with 1.3 M salt (50 mM Tris-Cl, 1.25 M NaCl, pH 8.5) supplemented with 15% isopropanol in absence and (Triangle)—presence of elevated temperature (50° C.).
Figure 17F:
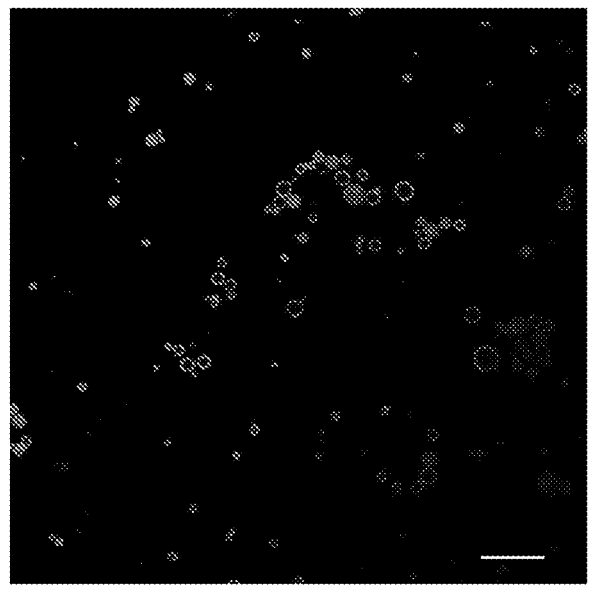
FIG. 17f shows unadsorbed pDNA found to be bound to the surface of Amikabeads-Q after desorption. Scale bar=100 μm.

The size of pDNA-Amikabead-Q aggregates were also determined after equilibration with different desorption buffers (listed in the Experimental section). Desorption resulted in lower aggregate sizes in all cases. In general, it was observed that the size of pDNA-Amikabead-Q aggregate decreased with increasing desorption of the biomacromolecule from the bead surface (FIG. 17e). Thus, desorption of the pDNA from Amikabead surface obviates extensive bridging, and therefore results in significant reduction in aggregate size. Undesorbed pDNA was found bound to the surface of Amikabeads (FIG. 17f). It is important to note that this aggregation behavior may be moot in case of well-packed chromatographic columns that may employ Amikabeads for pDNA separations.

In Situ Capture of DNA from Mammalian Cells

Cationic microparticles and membranes have been used for on-site capture of genomic DNA for polymerase chain reactions. It has been reported that chitosan coated beads that could extract DNA from lysed whole blood sample for PCR analyses. Here, Applicants investigated if Amikabeads P and Q could be employed for extracting DNA directly from mammalian cells.

Figure 9A:
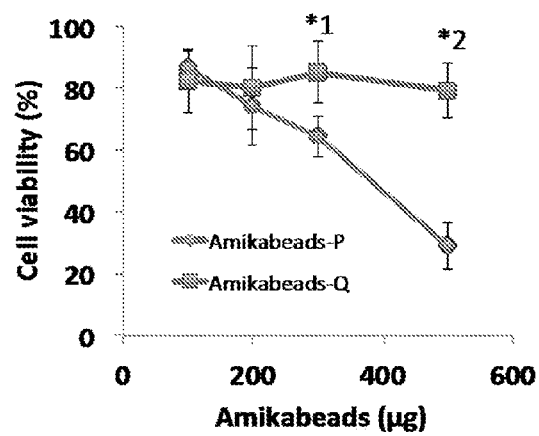
FIG. 9a graphically illustrates cell viability of PC3 human prostate cancer cells after exposure to different amounts of unmodified and quaternized Amikabeads for 24 hours as determined using the MTT assay (n=2). *1—statistical significance p=0.003 between cell viability of cells exposed to 300 μg Amikabeads-P and Q. *2—statistical significance p=0.00002 between cell viability of cells exposed to 500 μg Amikabeads-P and Q. Amikabeads-P (approximate diameter: ~12.±4 μm) and Amikabeads-Q (approximate diameter: ~11±6 μm). Students' t-test was used to determine statistical significance.

PC3 human prostate cancer cells were incubated with different amounts of Amikabeads-P and -Q in order to investigate their effect on viability following cell lysis; direct lysis mediated by the microbeads can facilitate extraction of DNA from cells. Amikabeads-P (500 µg, 24 hour incubation) resulted in loss of viability of ~80% of the cell population, as determined by the MTT assay (FIG. 9a, diamonds). The LC50 (amount required to reduce cell viability to 50%) value of Amikabeads-P was approximately 400 µg for PC3 prostate cancer cells under these experimental conditions.

Figure 9B:
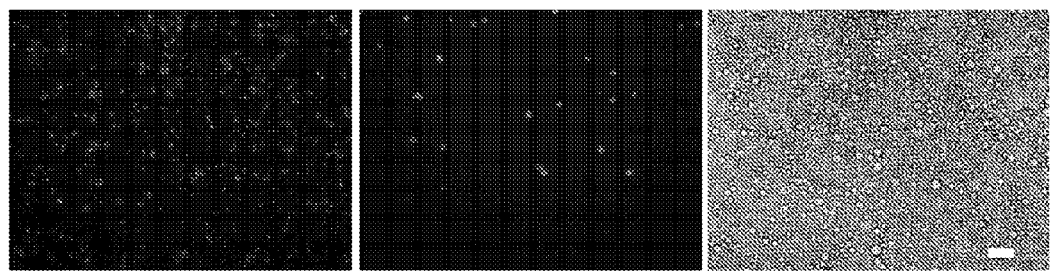
FIG. 9b shows Amikabeads-P (500 μg; approximate diameter: ~12±4 μm) exposed to 10,000 PC3 prostate cancer cells for 24 hours followed by live (green)-dead (red) staining. Scale bar=100 μm. Green fluorescence emission of Calcein inside the live cells was detected using 38 HE filter set (Excitation: 470/40; Emission: 525/50) and red fluorescence of nucleic acid bound-EthD-1 was detected using a 43 HE filter set (Excitation: 550/25; Emission: 605/70)
Figure 9C:
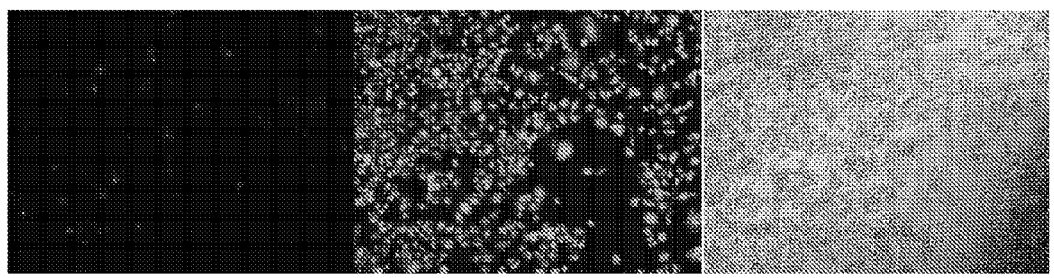
FIG. 9c shows 500 μg Amikabeads-Q (approximate diameter: ~11±6 μm) exposed to 10,000 PC3 prostate cancer cells for 24 hours followed by live (green)-dead (red) staining. Scale bar=100 μm. Green fluorescence emission of Calcein inside the live cells was detected using 38 HE filter set (Excitation: 470/40; Emission: 525/50) and red fluorescence of nucleic acid bound-EthD-1 was detected using a 43 HE filter set (Excitation: 550/25; Emission: 605/70)
Figure 18:
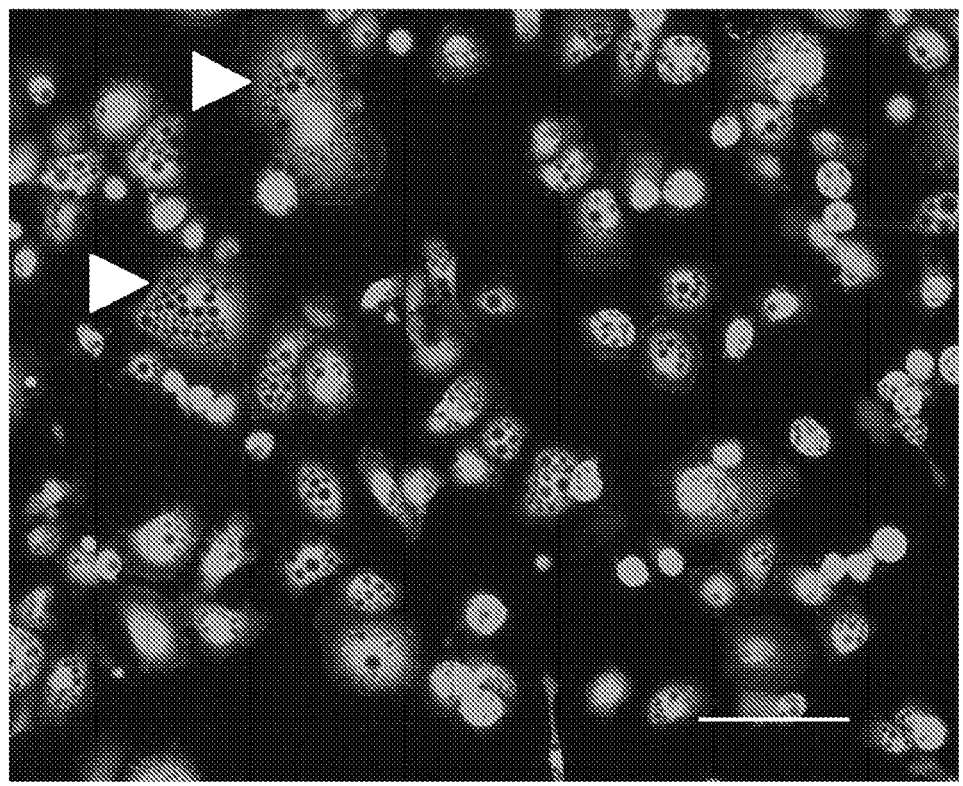
FIG. 18 shows Amikabeads-Q (500 μg; approximate diameter: 11±6 μm) exposed to 10,000 PC3 prostate cancer cells for 24 hours, followed by staining with Calcein AM. The beads on the surface of the PC3 prostate cancer cells can be seen as dark spheres. Green fluorescence emission of calcein inside the live cells was detected using 38 HE filter set (Excitation: 470/40; Emission: 525/50). Scale bar=100 μm.
Figure 19:
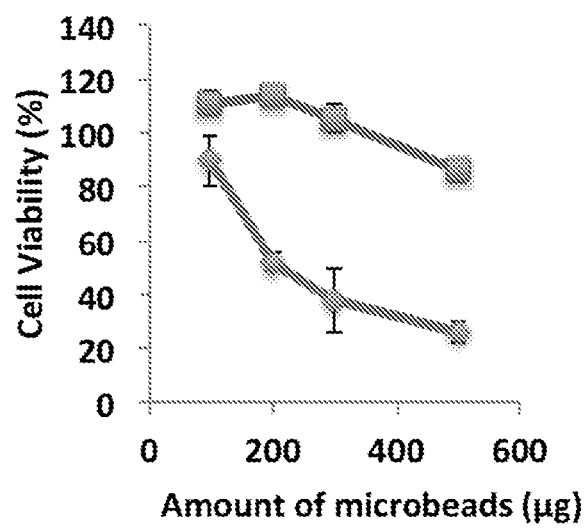
FIG. 19 graphically shows cell viability of PC3 human prostate cancer cells after treatment with different amounts of Amikabeads-P and -Q (Average diameters: Amikabeads-P: 12±4 μm Amikabeads-Q: 11±6 μm) for 6 hours in serum-free media, followed by 18 hours in serum containing RPMI media as determined using the MTT assay. Statistical test (Students' t-test) was used to test the statistical difference between the unmodified and quaternized Amikabeads. At all concentrations, the parental Amikabeads-P (squares) were significantly more toxic than the quaternized Amikabeads-Q (diamonds) (p<0.05)

In contrast, unlike Amikabeads-P, Amikabeads-Q did not induce significant cell death in PC3 cells even when amounts as high as 500 µg were employed (FIG. 9b, squares). These results from the MTT assay were further confirmed using LIVE/DEAD analyses, in concert with fluorescence microscopy (FIGS. 9a-b and FIG. 18). Amikabeads-P demonstrated significantly higher levels of red fluorescence compared to Amikabeads-Q, since cell lysis by the former results in damage and exposure of cellular DNA to the red-fluorescent ethidium homodimer-I dye. In all cases, the microbeads were seen in close proximity with the cells (FIGS. 9c and 19). Incubation of Amikabeads-P and -Q with PC3 cells in absence of serum proteins for 6 hours did not change the toxicity of parental (P) or quaternized (Q) Amikabeads (FIG. 19), indicating that serum proteins have minimal or no role in determining Amikabead cytotoxicity.

These results are along the lines of previous reports in literature that indicate reduced cytotoxicity of polymers after quaternization. For example, Brownlie et al. showed that quaternization of amines in polyethyleneimine (PEI) reduced its cytotoxicity by almost 4 fold in A431 lung cancer cells. It is understood that permanent positive charge of quaternized nitrogens unlike primary amines creates a solubilizing and hydrophilic environment that reduces interaction with the negative charges of the cell surface. Palermo et al. suggested that the interaction between polymers containing primary (1°), tertiary (3°) and quaternary ammonium groups (4°) with lipid membranes is dependent upon a combination of hydrophilicity combined with hydrogen-bonding effects. 4° ammonium containing compounds were found to be most hydrophilic, ineffective in partitioning into the hydrophobic core of the lipid-bilayer, less heamolytic than the other two polymers that caused dye leakage from dye-filled liposomes. Effective solvation on the 4 o ammonium groups were deemed the reason for its hydrophilic behavior. Applicants believe similar interaction could be responsible for cytotoxicity of Amikabeads-P and not Q.

Thus, although quaternization of Amikabeads-P led to microbeads with significantly lower toxicities, Amikabeads-P were employed for directly sequestering DNA following lysis of mammalian cells.

Fluorescence microscopy indicated in situ capture of cellular DNA in case of PC3 cells treated with 12±4 μm Amikabeads-P for 24 h (FIG. 10a). As seen in FIG. 8a, Amikabeads-P were able to simultaneously lyse cells, extract DNA molecules, and bind them. This activity of Amikabeads-P can have direct application in point-of-care testing 28, on-chip nucleic acid extraction and detection, and on-site/on-chip whole cell lysis and DNA/RNA capture for PCR reactions. Amikabeads-P, in absence of bound DNA, did not demonstrate any red fluorescence, which is along expected lines (FIG. 10b).

Amikabead Drug Conjugation

Figure 20:
FIG. 20 shows doxorubicin (Red) conjugated Amikabeads (pellet).

Primary amines and hydroxyls of Amikabeads-P were reacted with crosslinker 1,4-Cyclohexane dimethanol diglycidyl ether in excess to generate free epoxide groups. These free epoxide groups were further reacted and quenched with anticancer chemotherapeutic drug doxorubicin. Doxorubicin was found to bind to the beads and pellet down upon centrifugation (FIG. 20). Red color pellet was further analyzed using fluorescence microscopy to identify the location of the drug on the resin (data not shown). Table 2. shows the list of small molecules and anticancer drugs that can be attached to Amikabeads and Amikagel monolithic columns for novel mixed-mode pDNA chromatographic resins.

TABLE 2

| ID | Small molecules |
|---|---|
| 1 | Doxorubicin |
| 2 | Mitoxantrone |
| 3 | Daunomycin |
| 4 | Amonafide |
| 5 | Etoposide |
| 6 | Adenine |
| 7 | Guanine |
| 8 | Cyclosporamide |
| 9 | Vincristine |
| 10 | Netropsin |
| 11 | Furamidines |
| 12 | Ethidium bromide |
| 13 | Proflavine |
| 14 | Epirubicin |
| 15 | 8-Aminoacridine |
| 16 | Mitomycin |
| 17 | Distamycin |
| 18 | Idarubicin |
| 19 | Valrubicin |
| 20 | Pixantrone |
| 21 | Bleomycin |
| 22 | Methotrexate |

Amikagel Monolith Design

Figure 21A:
FIGS. 21a-b illustrate a cylindrical macroporous Amikagel based monoliths for plasmid DNA extraction, bone mimetic 3D surfaces etc.
Figure 21B:
Figure 21C:
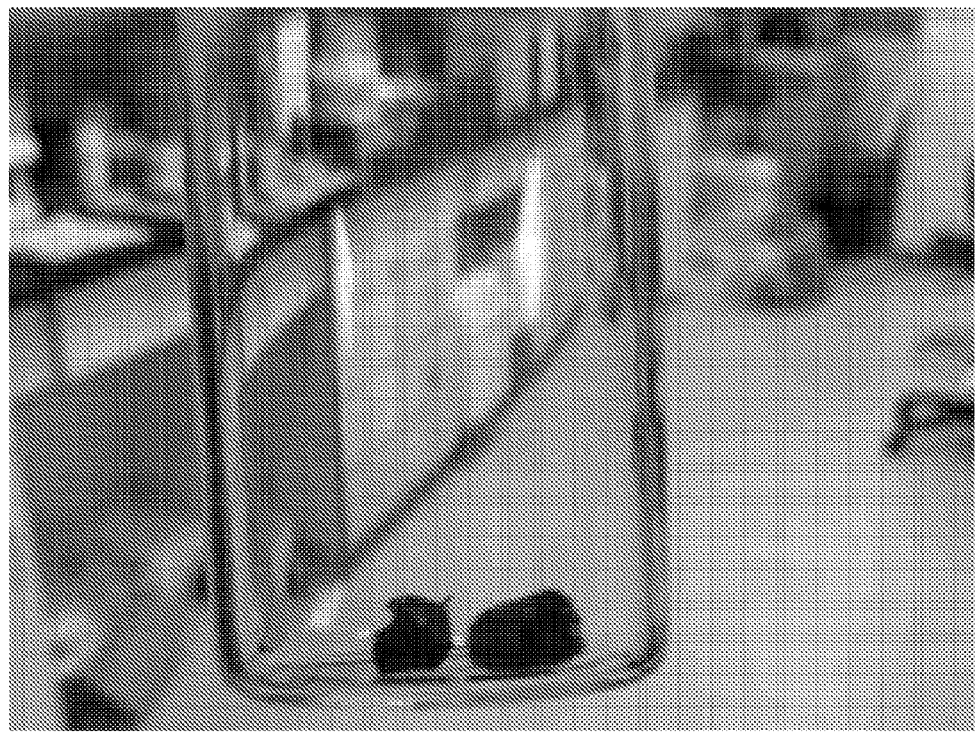
FIG. 21c illustrates a blue color which indicates positive for presence of amines on the surface of the gel (Ninhydrin assay). Scale bar=1 cm
Figure 22:
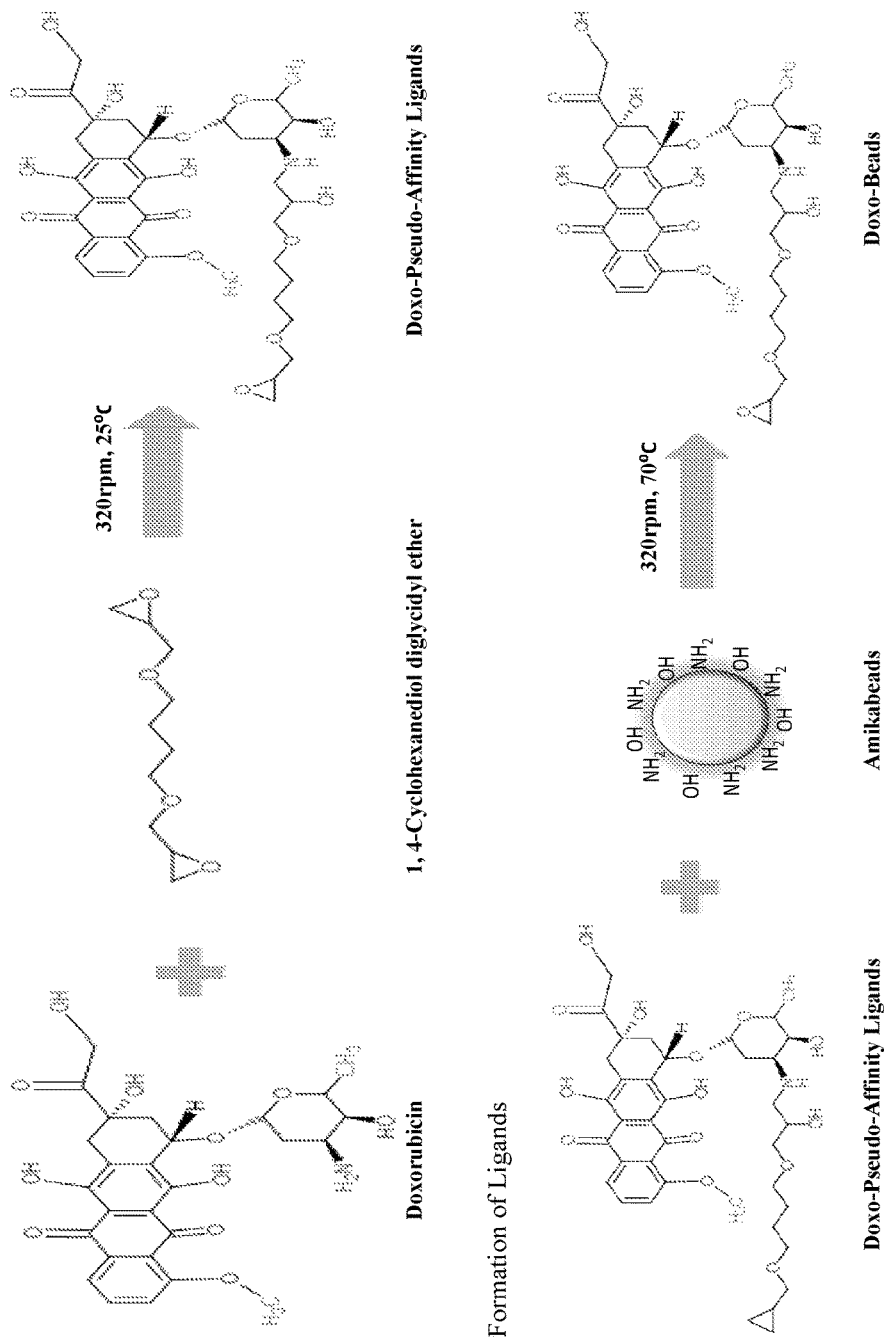
FIG. 22 illustrates the generation of Doxo-Beads.

Solution of Amikacin Hydrate was dissolved in DMSO and PEGDE was applied to a salt NaCl column and incubated at 40° C. for 24 hours. After 24 hours, the salt was dissolved in water leaving the macroporous monolith column as shown in FIG. 21(a-c).

Applicants have developed a novel anion-exchange resin material based on hydrogel microbeads ('Amikabeads') generated from amikacin and poly(ethylene glycol) diglycidyl ether, with an eye towards applications in DNA biotechnology. Parental (P) Amikabeads demonstrated a $Q_{max}$ of 44.5 μg pDNA/mg of the microbeads as determined from the Langmuir isotherm.

Near-complete recovery of pDNA was possible from Amikabeads-P using high salt concentrations, indicating electrostatic binding between the biomolecule and the microbeads. Quaternization of amines present in parental Amikabeads resulted in the formation of microbeads (Amikagels-Q), which demonstrated $Q_{max}$ values approximately 7-fold higher than those for Amikagels-P.

Desorption of the pDNA from these beads was not as efficient as Amikabeads-P, although, recovery could be significantly improved by using an organic modifier, isopropanol. Amikabeads-P were able to extract and bind cellular DNA following lysis of mammalian cells, indicating their use for in situ DNA extraction; Amikabeads-Q however, were not able to lyse cells and demonstrated lower cytotoxicities.

Applicants' results indicate that Amikabeads are a versatile platform, with multiple easily conjugable groups for several applications in DNA biotechnology ranging from purification to cellular DNA recovery.

Antibiotic aminoglycosides were mixed with cross-linker poly(ethyleneglycol) diglycidyl ether and were emulsified in mineral oil and detergent to yield parental amikagel microbeads (Amikabeads-P) of ~10 um after 25 minutes of mixing. Synthesized Amikabeads-P were extensively characterized using SEM, BET surface area and porosity measurement, optical microscopy, ninhydrin assay for amine quantification etc. After preparation, pGL4.5 plasmid was used to study its ability to bind plasmid DNA. Amikabeads-P were quaternized using glycidyl trimethyl ammonium chloride (GTMAC) to yield Amikabeads-Q to improve their cationicity towards plasmid DNA binding. Multiple chemotherapeutic anticancer drugs were conjugated to Amikabeads-P using crosslinkers to improve its plasmid DNA binding abilities. Amikabeads-P and Q were exposed to PC3 prostate cancer cells (ATCC-CRL 1435) and were used to extract their genomic DNA in-situ.

Pre-packed salt columns were wetted with aminoglycoside-PEGDE pre-gel DMSO solutions which were allowed to crosslink at 40° C. for 24 hours. After crosslinking, the salt was dissolved away to leave macroporous amikagels/amikagel monoliths. Macroporous amikagels/amikagel monoliths will be used for plasmid DNA binding, in-vitro models for prostate cancer cell culture in dormancy and relapse, mechanical reinforcement to mimic trabecular bone tissue, photothermally responsive material for wound healing etc.

In addition, amikabeads can be used as efficient tools for endotoxin binding and removal, substrate for peptide synthesis, substrate for chemical conjugation for ligands for pollutant removal, biomolecule binding and detection etc. Macroporous amikagels/amikagel monoliths can also be used for the same with increased surface area. In addition, they can be used for cell culture and tissue grafts to regenerate and replace tissues.

Gene therapy through plasmid DNA (pDNA hereafter) is being increasingly explored as a suitable therapeutic biologic for multiple diseases such as cancer, AIDS, Cystic fibrosis and DNA based vaccinations. Plasmid DNA is an extrachromosomal double stranded genetic material responsible for conferring selective advantages to bacteria such as antibiotic resistance and adaptability. These plasmid DNAs can be engineered to code for selective anticancer proteins that can induce death in cancer cells. Engineered plasmid DNA can then be grown in large quantities in bacterial cells before being extracted to pure form for therapeutic purposes.

Extraction of pharmaceutical grade plasmid DNA requires multiple downstream processing steps to get rid of unwanted cellular materials and genomic DNA. Anion-exchange chromatography, affinity-based chromatography, hydrophobic interaction chromatography, and size-exclusion and perfusion chromatography have been explored for purification of pDNA.

Two critical components of these chromatographic resins are the ligands used for binding the pDNA and the substrate to which the ligands are attached. Multiple ligands such as arginine, histidine, zinc fingers, triple-helix forming nucleotide sequences etc. have been explored as pseudo-affinity ligands for plasmid DNA binding. Stable substrates such as agarose and cross-linked agarose are commonly used. But these substrates are abundant in hydroxyl groups which are not as reactive as amine groups. To overcome these current challenges, here Applicants describe an invention of a completely new chromatographic resin where a crosslinked aminoglycoside-PEGDE hydrogel microbead and monolith substrate material and anticancer chemotherapeutic based ligands. Anticancer chemotherapeutic ligands interact with DNA via multiple modes such as electrostatic and hydrophobic interactions. Incorporation of such chemotherapeutics as ligands is hypothesized to improve binding capabilities of plasmid DNA via multi-modal interactions.

Applicants' chromatographic beads provide a high density amine rich resin with high cationicity. In addition, it has abundant highly conjugable groups such as hydroxyls and amines on its surface for further modification. Aminoglycoside-PEGDE hydrogel material was emulsified to create microbeads with extensive surface area for plasmid DNA binding. In addition, the primary amines were quaternized to generate a highly cationic substrate that could bind very high amounts of the cargo. Although microbeads provides a unique geometry for binding and extraction of plasmid DNA, numerous challenges such as efficient packing of chromatographic column and high fluid pressure during operation have to be dealt with. In order to overcome these challenges, Applicants designed macroporous amikagels/amikagel monoliths with varying pore sizes. These monoliths equipped with similar highly conjugable groups allows conjugation of pseudo affinity and multi-modal ligands that can be used for selective binding and purification of plasmid DNA.

The invention relates to a novel aminoglycoside based anion exchange chromatographic resin for plasmid DNA purification with a binding capacity of ~6 mg of plasmid DNA/mL of the resin. Abundant presence of easily conjugable groups make the resin highly desirable for further conjugations and modifications. The resin has been developed in two architectures namely microbeads and monolithic columns. Multiple ligands such as quaternary ammonium and mixed-mode ligands have been successfully attached to the resin for improvements in plasmid DNA binding.

The invention also relates to utilization of these novel beads for whole mammalian cell lysis for on-chip PCR reaction and point-of-care diagnostics.

A novel aminoglycoside based hydrogels have been generated in two different architectures of microbeads and monoliths for enhancing plasmid DNA binding. These resins provide a potential for further modifications with other ligands by the availability of multiple easily conjugable sites.

These resins have also been used for mammalian cell lysis and extraction of whole cell DNA. These can be used for on-chip PCR reactions and point-of-care diagnostics.

The material also provides a macroporous 3D substrate for cell culture and in vitro models of bone trabeculae etc.

The same material has been developed in multiple architectures for different applications. The presence of abundant easily conjugable groups such as amines and hydroxyls allows for further modification of the resin to cater the specific need of the application.

The invention also relates to the development of a macroporous hydrogel substrate for bone tissue engineering for prostate cancer dormancy and relapse. These macroporous hydrogels can be used for multiple applications including, but not limited to 3D in vitro model for cell culture for drug screening and discovery, stem cell differentiation substrates, tissue welding constructs and regenerative medicine.

Presence of a macroporous structure also potentiates its use towards bone mimetic material where macroporous amikagel can be used as bone trabecular mimetic. Macroporous amikagels can be strengthened using different reinforcing agents such as but not limited to carbon nanotubes, gold nanorods, hydroxyapatite to match the mechanical stiffness of bone trabecular region. These three dimensional macroporous gels provide unique substrate for binding of cells in their natural environment which two-dimensional substrates fail to provide. Applicants' mechanically reinforced macroporous gel will be used to study how the relapsing prostate cancer cells from dormancy will interact with the system. Co-culture of prostate cancer cells with osteoblasts and osteoclasts could provide a window to study unique tumor-osteal interactions in 3D environment, not possible with monolayer cells.

Synthetic procedure: Aminoglycoside amikacin and Poly (ethylene glycol) diglycidyl ether (PEGDE) mixture in 1:2 mole ratio was emulsified in Mineral oil and Span-80 surfactant (1% w/w) to give rise to ~10 um diameter microparticles/microbeads.

After crosslinking between Amikacin and PEGDE, the microbeads were collected and washed extensively to get rid of the mineral oil.

Washed microbeads were further conjugated with anticancer chemotherapeutic drug doxorubicin and quaternary ammonium group containing Glycidyl trimethyl ammonium chloride (GTMAC) for plasmid DNA binding.

Washed microbeads were also used for whole cell lysis and genomic DNA extraction by incubation of the microbeads with the cells. This invention provides a new tool for whole cell DNA extraction for on-chip PCR reactions and point-of-care diagnostics.

A cylindrical column filled with NaCl was wet with a solution containing Amikacin and PEGDE in DMSO. The salt column was left at 37° C. for 24 hours to allow gelation. After gelation, the construct was submerged in water to get rid of salt leaving behind a macroporous/monolithic amikagel construct. Macroporous monolith amikagel construct was further used for plasmid DNA binding, cell culture and surface conjugation of drugs.

The present invention also provides the methods of characterization, methods include at SEM, BET, Ninydrin assay, plasmid DNA adsorption and desorption etc, in vitro mammalian cell lysis and genomic DNA extraction.

The present invention has several advantages compare to the existing products. The merits include: High density amines on monoliths and microbeads for plasmid DNA binding, presence of multiple conjugable sites such as hydroxyls and amines for further modification. Chemotherapeutic drugs to bind plasmid DNA via electrostatic and hydrophobic interactions. Antibiotic based Macroporous gels for DNA binding Novel macroporous gels as bone mimetic surfaces for novel 3D cell culture of cancer cells (breast and prostate cancer) and stem cells (Embryonic stem cells and pluripotent stem cells).

In addition, Applicants have shown that the Amikabeads can be conjugated with Doxorubicin drug towards the development of anticancer chemotherapeutic based mixed mode chromatographic resins. Amikagel was also morphed into macroporous monolithic design to generate 3D scaffold for enhanced plasmid DNA binding, bone mimetic cell culture.

Preparation of Pseudo-Affinity Ligands from Anti-Cancer Drug: Preparation of Anti-Cancer Drug Solution. Doxorubicin (100 mg, 543 g/mol) was dissolved in 10 mL of Dimethyl sulfoxide (DMSO) followed by addition of 50 uL of triethylamine (TEA). The stock mixture of doxorubicin, DMSO and TEA (10 mg/mL) was stored in a 20 mL glass via at 4° C. and covered by aluminum foil for minimizing photoreaction.

Preparation of Pseudo Affinity Ligands. Doxorubicin was obtained from 4° C. storage and preheated at 35° C. for 5 mins. 10 mg of Doxorubicin was collected from the stock solution followed by addition of 1, 4-Cyclohexanediol diglycidyl ether (CHDDE) and TEA with a mole ratio of 1:3:5 in 20 mL glass vial. A certain amount of DMSO was added to the mixture in order to fulfill the total volume to be 2 mL. The glass container was covered by aluminum foil for minimizing photoreaction and the mixture was stirred with magnetic beads for 8 hours at 320 rpm to form pseudo-affinity ligands.

Formation of Conjugated Doxo-Beads. 1 mg of Amikabeads was collected from Amikabeads stock solution and washed by DMSO twice. Supernatant was decanted and microbeads were transferred to the prepared pseudo-affinity ligands solution. The solution was placed away from light and stirred at 320 rpm for 18 hours at 70° C. The diameter of conjugated doxo-beads were measured through microscope device and the image of beads were taken.

pDNA Binding to Conjugated Doxo-Beads. 1 mg of conjugated doxo-beads were incubated with 10,000 ng-120,000 ng of plasmid DNA (PGL 4.5) in 1 mL of 1.3M buffer I solution ($(NH)_4SO_4$ and 10mM Tris-Cl) at room temperature (25° C.) for 24 hours. All conjugated doxo-beads were first incubated with 10M HCl solution for 5 hours and washed with buffer I twice prior to binding with plasmid DNA. NanoDrop spectrophotometer was utilized to measure the pDNA content in the supernatant. Mass balance was performed to calculate the amount of pDNA adsorbed by conjugated doxo-beads. The data containing amount of pDNA adsorbed on the beads surface along with the pDNA content in equilibrium supernatant was fitted into linearized Langmuir Isotherm in order to determine the maximum binding capacity (Qmax) and Langmuir adsorption constant ($K_a$) for the conjugated doxo-beads. The linearzied Langmuir Isotherm was shown below:

$$\frac{C_e}{Q_e} = \frac{1}{Q_{max}} C_e + \frac{1}{Q_{max} * K_a}$$

where $Q_e$=amount of pDNA bound to the conjugated doxo-beads at equilibrium (ug/mg), $C_e$=concentration of pDAN in the solution at equilibrium (mg/L), $K_a$=Langumir adsorption constant (L/mg), $Q_{max}$=maximum amount of pDNA bound to the conjugated doxo-beads (ug/mg). $1/Q_{max}$ vs $C_e/Q_e$ was plotted in order to calculate the maximum binding capacity ($Q_{max}$) from slope and the Langmuir adsorption constant from intercept.

Desorption of Bound pDNA from Conjugated Doxo-Beads. Conjugated doxo-beads (~1 mg) were loaded with 75,000 ng-120,000 ng to ensure the beads was fully bound with pDNA. The desorption process was through two steps. Prior to the first step, the pDNA bound doxo-beads were firstly washed by buffer I in order to remove all the free pDNA content from supernatant. In the first step, the pDNA bound doxo-beads were immersed in 1 mL of buffer II solution (500 ul of buffer I and 500 ul of 10 mM Tris-Cl) for 24 hours; whereas in the second step, the pDNA bound doxo-beads were immersed in 1 mL of buffer III solution (10 mM Tris-CL) for 24 hours. The buffer III was refreshed after every 24 hours until no further pDNA was desorbed from doxo-beads. The amount of pDNA desorbed from both steps was measured via NanoDrop spectrophotometer.

Generation of Doxorubicin conjugated Amikabeads. We have previously demonstrated the development of parental aminoglycoside microbeads using emulsion polymerization. Next, we hypothesized that the conjugation of DNA binding anticancer drugs on parental aminoglycoside microbeads could improve their selectivity towards plasmid DNA in a mixture of pDNA and RNA. Doxorubicin a widely used anthracycline antibiotic anticancer drug which inhibits actively dividing cancer cells by interacting with the phosphate backbone of the DNA and the hydrophobic core. In order to conjugate doxorubicin on to the parental microbeads, we firstly conjugated the 1,4-butanediol diglycidyl ether and doxorubicin with excess of 1,4 butane diol diglycidyl ether (1:3) (FIG. 3.1a-b).

Figure 3:
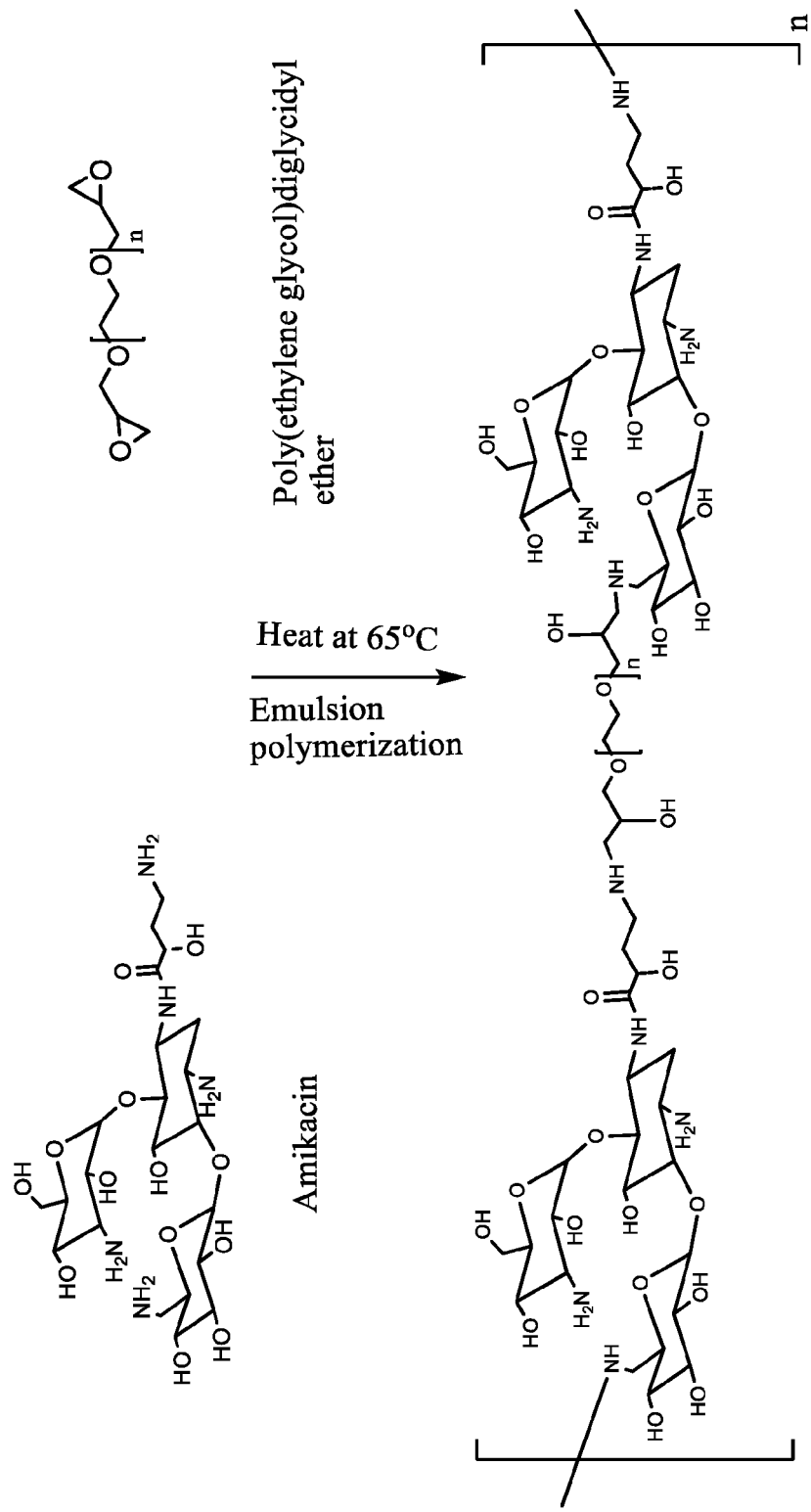
FIG. 3 recites a schematic of the reaction between amikacin hydrate and polyethylene glycol diglycidylether (PEGDE), resulting in the formation of Amikagel (hydrogel)

In our attempts to conjugate 1,4-butane diol diglycidyl ether on to the microbeads directly led to large scale aggregation of the microbeads (FIG. 3.2a). Hence, we firstly conjugated the pseudoaffinity ligand (doxorubicin in this case) to the crosslinker (1,4-butanediol diglycidyl ether in this case) and then conjugated the doxorubicin-1,4-butanediol diglycidyl ether moiety to the parental Amikabeads (FIG. 3.2b-c).

We believe our novel strategy of firstly linking pseudo-affinity ligand (doxorubicin in this case) to the crosslinker followed by their reaction to the microbeads can be used for multiple other applications of attaching ligands to the polymeric microbead surface while preventing large scale aggregation of the microbeads.

Using this strategy, we could generate large amounts of unaggregated doxorubicin conjugated aminoglycoside microbeads (amikabeads).

Loading plasmid DNA on doxorubicin conjugated Amikabeads. Loading plasmid DNA using 10 mM Tris-Cl did not cause any significant loading of plasmid DNA. Hence, we switched to Hydrophobic interaction loading of the plasmid DNA on to the resin. It is likely that after doxorubicin conjugation to the microbead surface, electrostatic interactions no longer dominate the binding. In HIC based loading of pDNA, high salt content forces pDNA unwinding and interaction of the hydrophobic nitrogenous bases of pDNA with the hydrophobic aminoglycoside resin. Under, 1.3M buffer I solution (($NH)_4SO_4$ and 10 mM Tris-Cl), pH 8.5 at 25 C, we noticed a very high binding capacity of pDNA on doxorubicin conjugated microbeads (Q-max=200,000 ng of pDNA/mg of resin) which was significantly higher than the parental beads (Q-max=40,000 ng of pDNA/mg of resin).

Elution of pDNA with 24 hour washes of 50% mixture of 1.3M buffer I solution (($NH)_4SO_4$ and 10 mM Tris-Cl) and 10 mM Tris-Cl solution each followed with 100% Tris-Cl allowed desorption and recovery of approximately 80-90% of loaded pDNA.

We show a novel strategy to bind anticancer drugs to the aminoglycoside microbeads without causing largescale aggregation of the beads. Doxorubicin conjugated aminoglycoside microbeads were found to load pDNA under high salt conditions (1.3M buffer I solution (($NH_4)_2SO_4$ and 10 mM Tris-Cl)). High recovery of pDNA was possible using low salt solutions. Our results show that anticancer drugs can be used as promising agents for pDNA binding and recovery.

While the preferred embodiments of the present invention have been illustrated in detail, it should be apparent that modifications and adaptations to those embodiments may occur to one skilled in the art without departing from the scope of the present invention.

The invention claimed is:

1. A method to prepare a macroporous column, comprising:
   providing a chromatographic column packed with salt;
   mixing an aminoglycoside and a cross-linker in an organic solvent;
   disposing said aminoglycoside/cross-linker/organic solvent in said chromatographic column;
   after said aminoglycoside reacts with said cross-linker to form a macroporous porous, cross-linked resin, adding water to said column to dissolve said salt;
   draining said water from said chromatographic column.

2. The method of claim 1, wherein said aminoglycoside is selected from the group consisting of Amikacin, Neomycin, Streptomycin, Tobramycin, Sisomicin, Paromomycin, Apramycin, Framecytin, Ribostamycin, Kanamycin, Arbekacin, Beckanamycin, Dibekacin, Astromicin, Spectinomycin, Hygromycin b, Gentamicin, Netilmicin, Isepamicin, and Verdamicin.

3. The method of claim 1, wherein said cross-linker comprises a di-epoxide.

4. The method of claim 1, wherein said cross-linker is selected from the group consisting of Poly (ethylene glycol) diglycidyl ether, Ethylene glycol diglycidyl ether, 1, 4-Cyclohexane dimethanol diglycidyl ether, Neopentyl glycol diglycidyl ether, 1,4- Butanediol diglycidyl ether, Resorcinol diglycidyl ether, Poly (propylene glycol) diglycidyl ether, Glycerol diglycidyl ether, Poly(ethylene glycol) diacrylate, Hexamethylene diacrylate, Neopentyl glycol diacrylate, 1,3-Butanediol diacrylate, 1,6-Hexanediol diacrylate, Bisphenol A ethoxylate diacrylate, Ethylene glycol diacrylate, 1,4-Butanediol, diacrylate, Glycerol 1,3-diglycerolate diacrylate, Neopentyl glycol diacrylate, Tetra(ethylene glycol) diacrylate, Poly(propylene glycol) diacrylate, Tri(ethyleneglycol) diacrylate, 1,6-Hexanediol ethoxylate diacrylate, and Neopentyl glycol propoxylate diacrylate.

5. A macroporous, cross-linked resin, formed by the process of:
   providing a chromatographic column packed with salt;
   mixing an aminoglycoside and a cross-linker in an organic solvent;
   disposing said aminoglycoside/cross-linker/organic solvent in said chromatographic column;
   after said aminoglycoside reacts with said cross-linker to form a macroporous porous, cross-linked resin, adding water to said column to dissolve said salt;
   draining said water from said chromatographic column.

6. The macroporous, cross-linked resin of claim 5, wherein said aminoglycoside is selected from the group consisting of Amikacin, Neomycin, Streptomycin, Tobramycin, Sisomicin, Paromomycin, Apramycin, Framecytin, Ribostamycin, Kanamycin, Arbekacin, Beckanamycin, Dibekacin, Astromicin, Spectinomycin, Hygromycin b, Gentamicin, Netilmicin, Isepamicin, and Verdamicin.

7. The macroporous, cross-linked resin of claim 5, wherein said cross-linker comprises a di-epoxide.

8. The macroporous, cross-linked resin of claim 5, wherein said cross-linker is selected from the group consisting of Poly (ethylene glycol) diglycidyl ether, Ethylene glycol diglycidyl ether, 1, 4-Cyclohexane dimethanol diglycidyl ether, Neopentyl glycol diglycidyl ether, 1,4- Butanediol diglycidyl ether, Resorcinol diglycidyl ether, Poly (propylene glycol) diglycidyl ether, Glycerol diglycidyl ether, Poly(ethylene glycol) diacrylate, Hexamethylene diacrylate, Neopentyl glycol diacrylate, 1,3-Butanediol diacrylate, 1,6-Hexanediol diacrylate, Bisphenol A ethoxylate diacrylate, Ethylene glycol diacrylate, 1,4-Butanediol diacrylate, Glycerol 1,3-diglycerolate diacrylate, Neopentyl glycol diacrylate, Tetra(ethylene glycol) diacrylate, Poly(propylene glycol) diacrylate, Tri(ethyleneglycol) diacrylate, 1,6-Hexanediol ethoxylate diacrylate, and Neopentyl glycol propoxylate diacrylate.

9. A method to form microbeads comprising an aminoglycoside moiety, comprising:
   polymerizing a reaction mixture comprising an aminoglycoside and a cross-linker;
   prior to gellation, disposing said reaction mixture into heated mineral oil;
   collecting said microbeads by centrifugation.

10. The method of claim 9 wherein said aminoglycoside comprises amikacin.

11. The method of claim 9, wherein said cross-linker comprises polyethylene glycol diexpoxide.

12. The method of claim 9, wherein said reaction tore comprises a weight ratio of 1:2 amikacin to PEGDE.

13. The method of claim 9, wherein said heated mineral oil is maintained at a temperature of 65° C. with constant stirring at 260 rpm.

14. The method of claim 9, wherein said reaction mixture comprises a surfactant.

15. The method of claim 9, further comprising prior to forming said reaction mixture, reacting said amikacin with glycidyl trimethyl ammonium chloride.

16. Microbeads comprising an aminoglycoside moiety, formed by the process of:
   polymerizing a reaction mixture comprising an aminoglycoside and a cross-linker;
   prior to gellation, disposing said reaction mixture into heated mineral oil;
   collecting said microbeads by centrifugation.

17. The microbeads of claim 16, wherein said aminoglycoside comprises amikacin.

18. The microbeads of claim 16, wherein said cross-linker comprises polyethylene glycol diexpoxide (PEGDE).

19. The microbeads of claim 16, wherein said reaction mixture comprises a weight ratio of 1:2 amikacin to PEGDE.

20. The microbeads of claim 16, wherein said heated mineral oil is maintained at a temperature of 65° C. with constant stirring at 260 rpm.

21. The method of claim 16, wherein said reaction mixture comprises a surfactant.

22. The method of claim 16, further comprising prior to forming said reaction mixture, reacting said amikacin with glycidyl trimethyl ammonium chloride.

* * * * *

UNITED STATES PATENT AND TRADEMARK OFFICE
CERTIFICATE OF CORRECTION

PATENT NO. : 10,232,345 B2
APPLICATION NO. : 15/547173
DATED : March 19, 2019
INVENTOR(S) : Kaushal Rege, Taraka Sai Pavan Grandhi and Thrimoorthy Potta Page 1 of 1

It is certified that error appears in the above-identified patent and that said Letters Patent is hereby corrected as shown below:

In the Claims

Claim 12, Line 35, "reaction tore" should read --reaction mixture--

Signed and Sealed this
Sixteenth Day of July, 2019

Andrei Iancu
*Director of the United States Patent and Trademark Office*